(12) United States Patent
Zhu

(10) Patent No.: US 9,492,176 B2
(45) Date of Patent: Nov. 15, 2016

(54) CLAMPING AND LIGATION DEVICE

(76) Inventor: Jian Zhu, Guangdong (CN)

( * ) Notice: Subject to any disclaimer, the term of this patent is extended or adjusted under 35 U.S.C. 154(b) by 345 days.

(21) Appl. No.: 14/234,643

(22) PCT Filed: Aug. 30, 2012

(86) PCT No.: PCT/CN2012/080793
§ 371 (c)(1),
(2), (4) Date: Jan. 24, 2014

(87) PCT Pub. No.: WO2013/067844
PCT Pub. Date: May 16, 2013

(65) Prior Publication Data
US 2014/0171974 A1 Jun. 19, 2014

(30) Foreign Application Priority Data

Nov. 11, 2011 (CN) .......................... 2011 1 0358591

(51) Int. Cl.
*A61B 17/122* (2006.01)
*A61B 17/128* (2006.01)
*A61B 17/29* (2006.01)

(52) U.S. Cl.
CPC ........... *A61B 17/122* (2013.01); *A61B 17/128* (2013.01); *A61B 17/1227* (2013.01); *A61B 17/1285* (2013.01); *A61B 2017/2905* (2013.01)

(58) Field of Classification Search
CPC .............. A61B 17/122; A61B 17/128; A61B 17/1285; A61B 17/12; A61B 17/1227; A61B 2017/12004
USPC ........ 606/139, 142, 143, 151, 157, 158, 219
See application file for complete search history.

(56) References Cited

U.S. PATENT DOCUMENTS

| | | | | |
|---|---|---|---|---|
| 3,958,576 A * | 5/1976 | Komiya | ............... | A61B 17/083 24/456 |
| 5,766,184 A * | 6/1998 | Matsuno | .......... | A61B 17/00234 604/15 |
| 5,766,189 A * | 6/1998 | Matsuno | .............. | A61B 17/128 606/139 |
| 6,814,742 B2 * | 11/2004 | Kimura | ............... | A61B 17/083 606/142 |
| 6,991,634 B2 * | 1/2006 | Sugiyama | ............ | A61B 17/122 606/142 |
| 7,108,699 B2 * | 9/2006 | Kobayashi | ......... | A61B 17/1285 606/142 |
| 7,494,461 B2 * | 2/2009 | Wells | ................... | A61B 17/122 600/104 |
| 7,727,247 B2 * | 6/2010 | Kimura | .............. | A61B 17/1222 606/142 |
| 7,854,739 B2 * | 12/2010 | Satake | ............... | A61B 17/1285 606/142 |
| 8,172,859 B2 * | 5/2012 | Matsuno | .............. | A61B 17/122 606/142 |

(Continued)

FOREIGN PATENT DOCUMENTS

| | | |
|---|---|---|
| CN | 101087564 B | 6/2010 |
| WO | 03030746 A | 4/2003 |

*Primary Examiner* — Todd E Manahan
*Assistant Examiner* — Charles Wei

(57) ABSTRACT

A clamping and ligation device, comprising a ligation unit (10), a conveying unit (20), a protective sleeve (30), a connecting unit (40), a operation unit (50), and a traction unit (60); the connecting unit (40) connects the conveying unit (20) with the ligation unit (10), and can be disengaged to separate the conveying unit (20) from the ligation unit (10); the traction unit (60) controls the ligation unit (10) via push and pull movement; the end of the traction unit (60) connected to the ligation unit (10) is breakable, so that the traction unit (60) can be broken away from the ligation unit (10) under a definite force; the protective sleeve pipe (30) can accommodate the whole ligation unit (10) therein, thus, during endoscope penetration, avoiding the damage to the endoscope tube wall and the increase of penetration force.

23 Claims, 34 Drawing Sheets

(56) References Cited

U.S. PATENT DOCUMENTS

| | | | | |
|---|---|---|---|---|
| 8,551,119 B2* | 10/2013 | Kogiso | A61B 17/122 | 606/142 |
| 8,663,247 B2* | 3/2014 | Menn | A61B 17/122 | 606/142 |
| 8,939,997 B2* | 1/2015 | Martinez | A61B 17/08 | 606/1 |
| 9,072,520 B2* | 7/2015 | Terada | A61B 17/1222 | |
| 2002/0133178 A1* | 9/2002 | Muramatsu | A61B 17/1285 | 606/142 |
| 2003/0069592 A1* | 4/2003 | Adams | A61B 17/122 | 606/142 |
| 2004/0133228 A1* | 7/2004 | Bayer | A61B 17/00008 | 606/190 |
| 2005/0187574 A1* | 8/2005 | Senzaki | A61M 25/1002 | 606/194 |
| 2008/0140089 A1* | 6/2008 | Kogiso | A61B 17/122 | 606/142 |
| 2008/0306491 A1* | 12/2008 | Cohen | A61B 17/122 | 606/142 |
| 2010/0152753 A1* | 6/2010 | Menn | A61B 17/122 | 606/158 |
| 2011/0046651 A1* | 2/2011 | Cohen | A61B 17/1227 | 606/157 |
| 2012/0109160 A1* | 5/2012 | Martinez | A61B 17/08 | 606/142 |
| 2013/0123818 A1* | 5/2013 | Li | A61B 17/122 | 606/157 |
| 2015/0190136 A1* | 7/2015 | Cohen | A61B 17/122 | 606/143 |

* cited by examiner

CLAMPING AND LIGATION DEVICE

FIELD OF THE INVENTION

The present invention relates to the technical field of medical devices, more particularly to a clamping and ligation device and a ligation method applying the clamping and ligation device.

BACKGROUND OF THE INVENTION

In medical treatment, a clamping device and an endoscope are used together, to clamp and ligate the living organisms in the living body via the clamping device.

In the prior art, PCT patent application 2003/030746A1 discloses a medical device, which sends a clamping device to the target area by using an endoscope, for hemostasis of blood. The medical device includes a closable clamp for blood vessels hemostasis, locking devices, control lines, a cover and a handle with a start trigger. One end of a control line is arranged in the cover, the other end of the control line is J-shaped hook, hooking an opening on the bottom of a clip of the clamp, to achieve the connections with the clamp. The cover is pushed to move the control line, and then the clip of the clamp is opened or closed. The outer end of the cover is connected with a case, and the end of the case is connected to the locking device, and the control line runs through the case and the locking device. An end of the locking device is provided with a pawl, when the control lines are pulled back and the clip is pulled back, the pawl could be stuck in a locking hole of the leg, so that the clip remains closed and locked. After ligation, the control line is continued to be pulled back, such that the J-shaped hook becomes straight, the control line breaks from the clip; Meanwhile, under the function of a fastener and a removing device for removing the fastener, the case breaks from the locking device; finally the locking device and the clamp remain in the organism.

However, regarding the ligation device in the above PCT patent application, since the pawl of the locking device is stuck in a locking hole of the leg so as to lock the clamp, the clamp is not completely contained in the locking device (and the case), and an end of the clamp will be exposed outside. Thus, when the ligation device runs through the channel of the endoscopic tube, there exists the danger that the end of the clamp will damage the inner wall of the endoscopic tube, or the end of the clamp will be stuck in the inner wall, so that a very large inserting force for the ligation device is required, and the difficulty of the operation is increased.

To overcome these defects, the Chinese Patent No. 200580044431.7 provides a ligation apparatus, including a sheath means for running through a channel of an endoscope and inserting into a body cavity, a clip is housed in one end of the sheath; an operating line for controlling the clamp runs through the sheath. The clamp is formed by a claw thereof embedding in a substantially cylindrical body portion of a pressing member. The clamp can be completely accommodated in the sheath by a special mechanism, and the end of the clamp is not exposed outside, thus the danger that the ligation device damages the channel when the ligation device runs through the endoscope or the inner tube of the living body is avoided, and a large inserting force for the ligation device when the end of the clamp is stuck in the channel is also avoided.

However, in the ligation apparatus of the above Chinese Patent, since the pressing member is provided with a flexible wing, before the clamp is sent out of the sheath, the flexible wings is in folded state, but when the clamp is sent out of the sheath, the flexible wings is in expanded state, (being used for providing a supporting point for pulling back the operation wire), and therefore the clamp is not accommodated in the sheath any more. Thus, if the surgical operation fails, the clamp could not be recycled for operation; moreover, pulling back the lever hard, will make the clamp to stay in the body cavity without serving any function, which not only causes waste of the clamp, but also brings in harm owing to the clamp remaining in the body.

In addition, in the above PCT patent 2003/030746A1, the J-shaped hook of the control line is stuck in the opening at the bottom of the leg, when subjected to longitudinal tension, the J-shaped hook is blocked by the wall of the opening in the process of being straightened, the J-shaped hook requires a larger force in this process, which increases the difficulty of operation and wastes time; and the J-shaped hook only can be straightened after the ligation part is closed, if the J-shaped hook is prematurely straightened, then the bottom portions of the clamp could not be combined together, thus effect of the ligation is affected, and the operation time is extended. Meanwhile, the fastener and the removing device for removing the fastener have complicated structures, so achieving the separation function is required a larger force, and the operation time is longer and the difficulty of the operation is increased.

Accordingly, there need an improved clamping and ligation device and a ligation method applying the clamping and ligation device to overcome the drawback.

SUMMARY OF THE INVENTION

The purpose of the present invention is to provide a clamping and ligation device, which could not only achieve the ligation unit being contained in the protective sleeve completely, but also achieve the ligation unit being pushed and pulled repeatedly, so that an ideal effect of the ligation is obtained; furthermore, the clamping and ligation device could be disintegrated effectively and quickly after the operation is finished, and part of the clamping and ligation device which remains in the living body possesses simple structure and is easy to be discharged.

In order to achieve the above purpose, the present invention provides a clamping and ligation device, including:

a ligation unit, which comprises a ligation component and an accommodation tube in which the ligation component is housed, the ligation unit being capable of remaining in a digestive tract of a living body for some time and then falling off automatically to be excreted from the living body, the ligation component comprising at least two clamping arms arranged symmetrically, the clamping arms being connected to each other at the bottom thereof to form a joint part of the ligation component;

a conveying unit, which is connected to an end of the accommodation tube, the conveying unit comprising a flexible tube and a sleeve which is mounted on an end of the flexible tube, the sleeve being engaged with the accommodation tube to form a junction where a wall of the sleeve overlaps a wall of the accommodation tube, each of the sleeve and the accommodation tube has a connection hole and the connecting holes are aligned at the junction;

a protective sleeve, which surrounds the conveying unit and the ligation unit, the conveying unit and the ligation unit being moved radially in the protective sleeve, and the ligation unit being accommodated completely in the protective sleeve;

a connecting unit, which comprises at least a leg, which has a contact portion formed at the bottom thereof and a bent portion at the top thereof, the bent portion being inserted into the connection hole formed on the conveying unit and the accommodation tube, so as to connect the conveying unit and the accommodation tube together, and the bent portion being disengaged from the connection hole when the leg is subjected to a longitudinal force;

an operation unit, which comprises a main body, an operation rod and an operation block controlling the movement of the operation rod, and a back end of the flexible tube being mounted on the main body of the operation unit; and a traction unit, running through and moving longitudinally in the conveying unit and the accommodation tube, one end of the traction unit being connected to the joint part of the ligation component, the other end being connected to the operation rod of the operation unit, and the traction unit controlling the movement of the ligation component by the operation block; the end of the traction unit which is connected to the joint part of the ligation component being detachable from the joint part, the traction unit comprising an abutment part; when the traction unit is pulled back, the abutment part is abutted against the contact portion of the connecting unit, then the bent portion of the leg is disengaged from the connection hole under the pull force.

Preferably, the sleeve of the conveying unit has a stepped hole, a step is formed in a circumferential direction on an end of the accommodation tube to match with the stepped hole, and the stepped hole is engaged with the step to make a wall of the sleeve to overlap a wall of the accommodation tube.

Preferably, a step structure is formed in the circumferential direction in the sleeve of the conveying unit, a stepped hole is formed on an end of the accommodation tube to match with the step structure, and the stepped hole is engaged with the step structure to make a wall of the sleeve to overlap a wall of the accommodation tube.

Preferably, the flexible tube consists of flexible steel sheet or steel wire.

Preferably, the flexible tube consists of woven wire net or composites composed of woven wire net and plastic.

Preferably, the protective sleeve is flexible.

Preferably, the protective sleeve consists of PE, PP or PVC material.

Preferably, the ligation component is made by bending a single piece of material and forms two clamping arms, and two clamping arms are connected to each other to form the joint part of the ligation component.

Preferably, a clamping head is formed on the top of the clamping arm.

Preferably, the end of the traction unit which is connected to the ligation unit is a hook, which hooks the joint part of the ligation component; the hook deforms to detach from the joint part of the ligation component under a certain force.

Preferably, the traction unit includes a first traction rod and a second traction rod which is connected to the first traction rod longitudinally to form an overlap part, and the overlap part forms a step part which forms an abutment part.

Preferably, the connecting unit is made by bending a single piece of material, and comprises two legs.

Preferably, two said legs are symmetrical and each has a bent portion at the top.

Preferably, two said legs are symmetrical and only one of them has a bent portion at the top.

Preferably, the connecting unit includes at least three legs.

Preferably, the connecting unit includes a leg.

Preferably, the connecting unit is a U-shaped structure made by bending a single piece of material, two arms of the U-shaped structure form two legs of the connecting unit, the bent portion is formed at the top of each leg; the bending portion in the middle of U-shaped structure forms the contact portion.

Preferably, the protective sleeve includes at least two channels, and the conveying unit and the ligation unit run through one of the channels.

Preferably, the clamping and ligation device further includes a stopper unit, which is removably mounted on one end of the flexible tube which is connected to the main body of the operation unit, the length of the stopper unit in a longitudinal direction of the flexible tube is greater than the length of the ligation unit in the longitudinal direction when the ligation component is folded, and the ligation unit is completely contained in the protective sleeve when the stopper unit is mounted on the flexible tube.

Preferably, the stopper unit includes at least two flexible stopper arms which move in the same or in the opposite direction, each of the flexible stopper arms has a limit recess formed thereon to match with the flexible tube, and all the limit recesses form a limit hole for limiting the position of the flexible tube.

Preferably, the stopper unit includes three flexible stopper arms which are arranged in row and coupled to each other at the bottom, the middle one of the flexible stopper arms moves in a certain direction, and the other two of the flexible stopper arms move in the opposite direction to the middle one, each of the flexible stopper arms has a limit recess formed thereon to match with the flexible tube, and three said limit recesses form a limit hole for limiting the position of the flexible tube.

Preferably, at least one separate plate is arranged on one end of the accommodation tube to separate the clamping arms, and the accommodation tube is provided with a chamfer to help the ligation component to spread and fold.

Another purpose of the present invention is to provide a ligation method applying the above clamping and ligation device, it can guarantee that the ligation component inserts into the endoscope without damaging the wall of the endoscope and the inserting force is smaller, and the ligation component could be pushed and pulled repeatedly until an ideal effect of the ligation is obtained, furthermore, the ligation component could be disintegrated effectively and simply from other parts of the clamping and ligation device, and the part which remains in the living body possesses simple structure and is easy to be discharged.

In order to achieve the above purpose, the present invention provided a ligation method applying the above clamping and ligation device, which includes the following steps:

(1) folding the ligation component of the clamping and ligation device in the accommodation tube, and containing the ligation unit in the protective sleeve completely;

(2) passing the clamping and ligation device through a channel which can hold an endoscope, and then to the operating position, wherein the operation unit, a back end of the flexible tube, and a back end of the protective sleeve are exposed outside the living body;

(3) pushing the whole operation unit, and the ligation unit is pushed out from the protective sleeve;

(4) pushing the operation block, the operation block pushing the operation rod, and then the traction unit moving forward to push the ligation component spread out of the accommodation tube, and the position which is need to be ligated is arranged between the clamping arms;

(5) pulling back the operation block, and then the ligation component is pulled into the accommodation tube and is folded therein;

(6) repeating steps (4)-(5) when the ligation is not ideal, until a desired effect is achieved; and (7) continue to pull back the operation block until the end of the traction unit which is connected to the ligation unit is detached from the ligation unit; the abutment part of the traction unit is abutted against the contact portion of the connecting unit, causing the bent portion of the leg of the connecting unit to disengage from the connection holes and causing the accommodation tube to detach from the conveying unit.

Preferably, the clamping and ligation device further includes a stopper unit, which is removably mounted on one end of the flexible tube which is connected to the operation unit, the length of the stopper unit in a longitudinal direction of the flexible tube is greater than the length of the ligation unit in the longitudinal direction when the ligation component is folded, and the ligation unit is completely contained in the protective sleeve when the stopper unit is mounted on the flexible tube; during step (1), mounting the stopper unit on the flexible tube, and the ligation unit and the conveying unit is contained in the protective sleeve; during step (2), dismounting the stopper unit after the clamping and ligation device pass through the corresponding channel of the endoscope.

The advantage of the present invention is that: the clamping and ligation device according to the present invention, could achieve the ligation unit being contained in the protective sleeve completely, so that the ligation component will not damage the wall of the endoscope when inserting into the endoscope and the inserting force is smaller; furthermore, the ligation unit could be pushed and pulled repeatedly, and the ligation component could be outspreaded repeatedly, so that the ligation component could be pulled back to repeat the operation when the an ideal effect of ligation is not obtained, until the ideal ligation effect is obtained; moreover, the clamping and ligation device could be disintegrated effectively after the operation is finished, and the part of the clamping and ligation device which remains in the body possesses simple structure and is easy to be discharged. The ligation method applying the clamping and ligation device according to the present invention also could achieve the above technical effects.

DETAILED DESCRIPTION OF ILLUSTRATED EMBODIMENTS

The embodiments of the present invention are disclosed in detail by combining with figures below.

Figure 1:
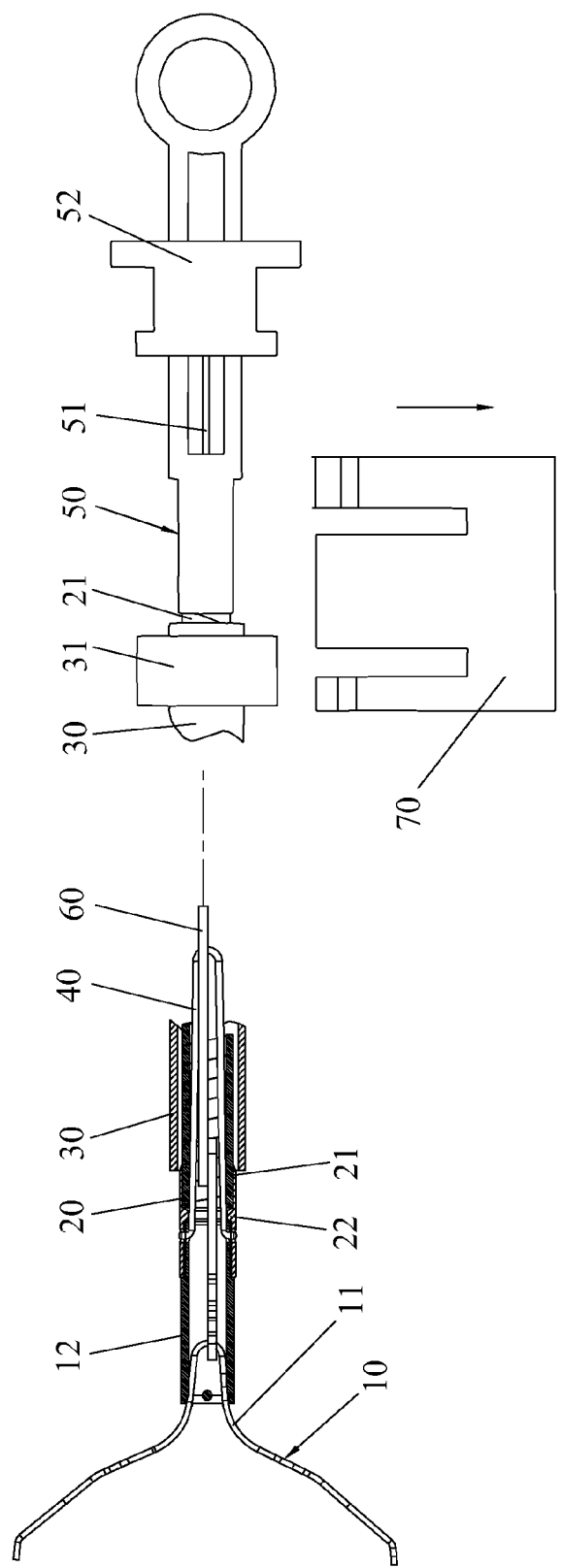
FIG. 1 is a schematic diagram showing a clamping and ligation device without a stopper unit according to an embodiment of the present invention, with a ligation component of the ligation unit being in expanding state.
Figure 2:
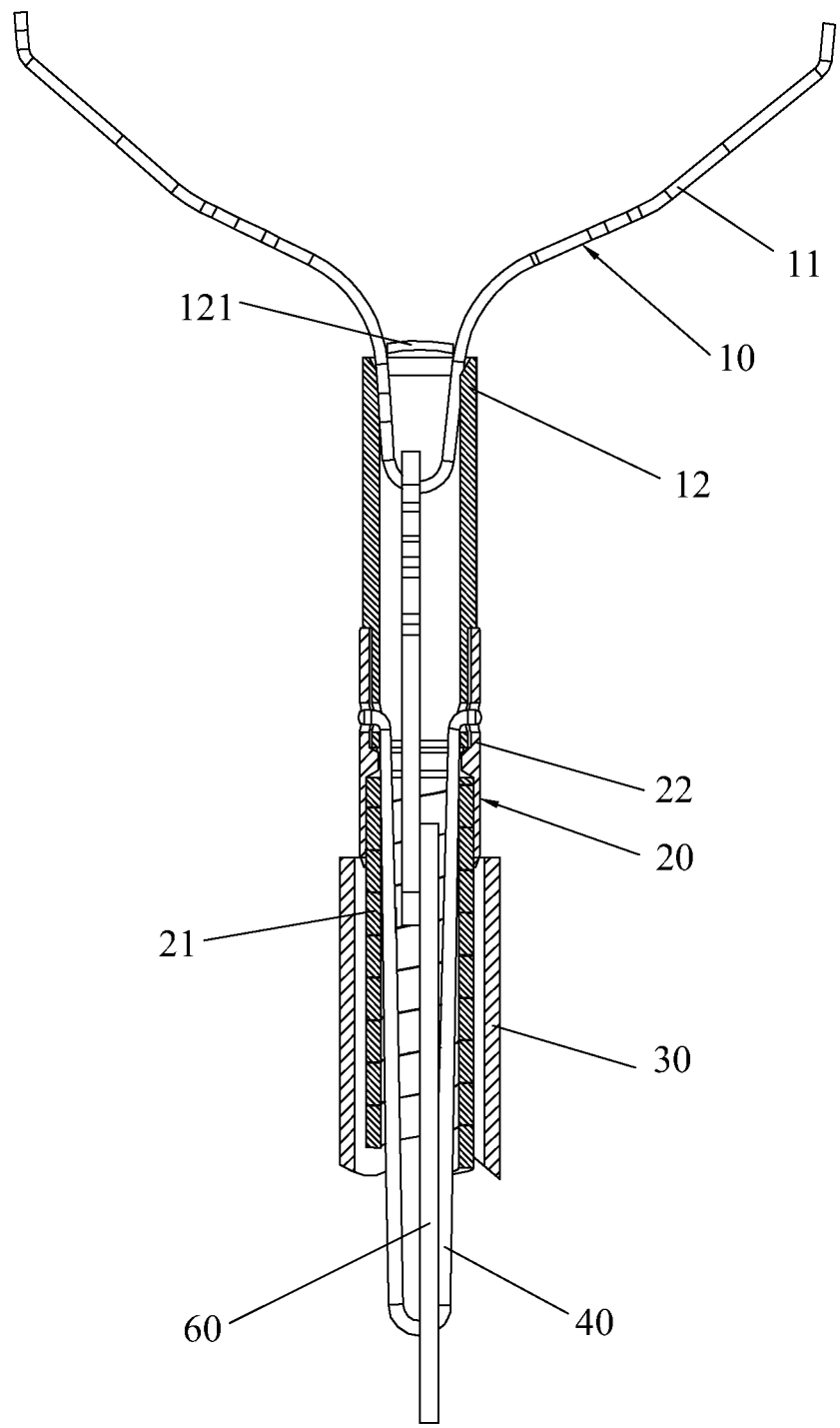
FIG. 2 is a partial schematic diagram of the clamping and ligation device shown in FIG. 1, showing a protective sleeve, the ligation unit, a connecting unit and a traction unit, with the ligation component of the ligation unit being in expanding state.
Figure 3:
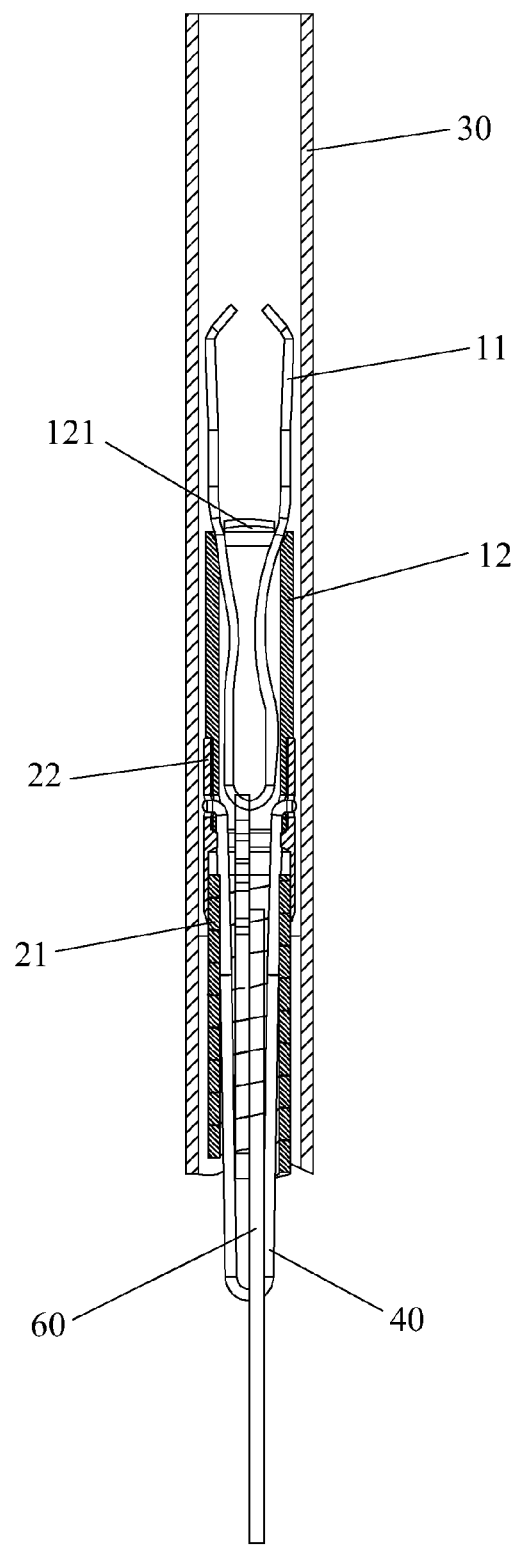
FIG. 3 is a partial schematic diagram of the clamping and ligation device shown in FIG. 1, showing the protective sleeve, the ligation unit, the connecting unit and the traction unit, with the ligation component of the ligation unit being in folding state.

FIG. 1 demonstrates a whole structure of the clamping and ligation device according to an embodiment of the present invention. Referring to FIGS. 1-3, the clamping and ligation device includes a ligation unit 10, a conveying unit 20, a protective sleeve 30, a connecting unit 40, an operation unit 50, and a traction unit 60. Below is a detailed description.

Ligation Unit

A ligation unit 10 includes a ligation component 11 and an accommodation tube 12 in which the ligation component 11 is housed; the ligation unit 10 could be remained in a digestive tract of a living body for some time and then falls off automatically to excrete from the living body. The ligation component 11 includes at least two clamping arms arranged symmetrically, and the clamping arms are connected to each other at the bottom thereof to form a joint part of the ligation component.

Figure 4:
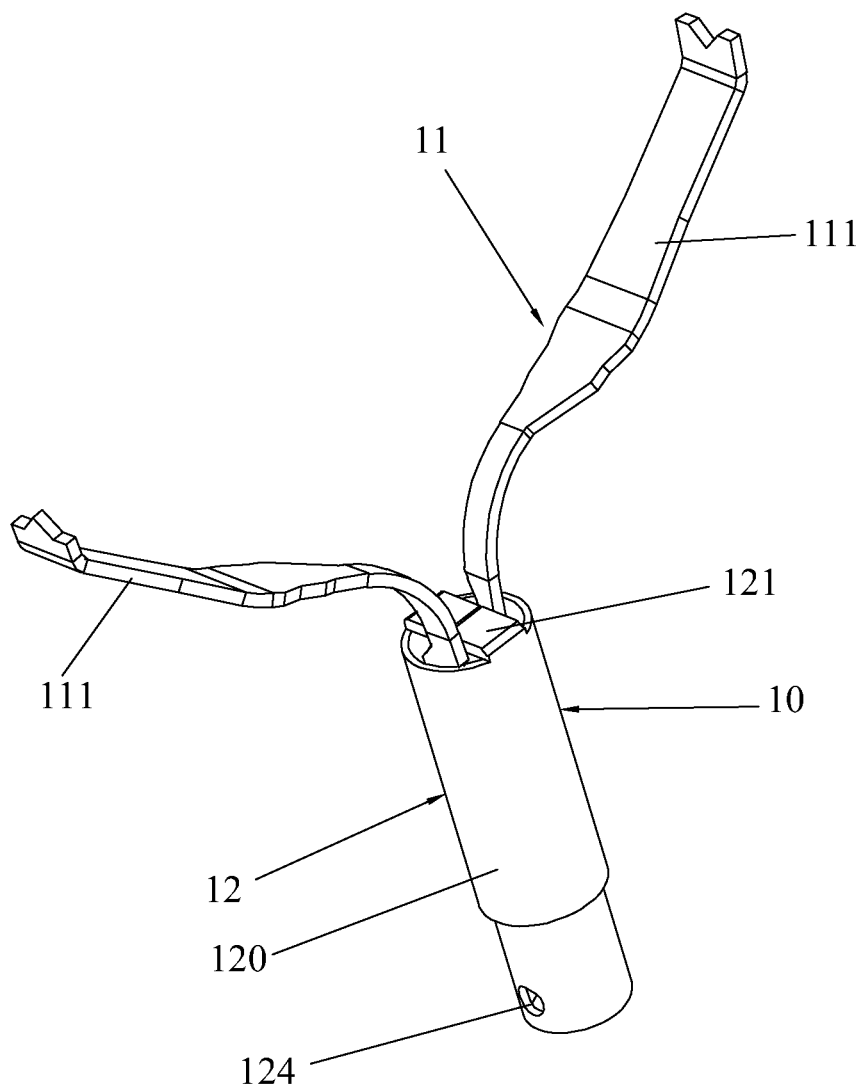
FIG. 4 is a stereogram showing the ligation unit of the clamping and ligation device shown in FIG. 1.
Figure 5:
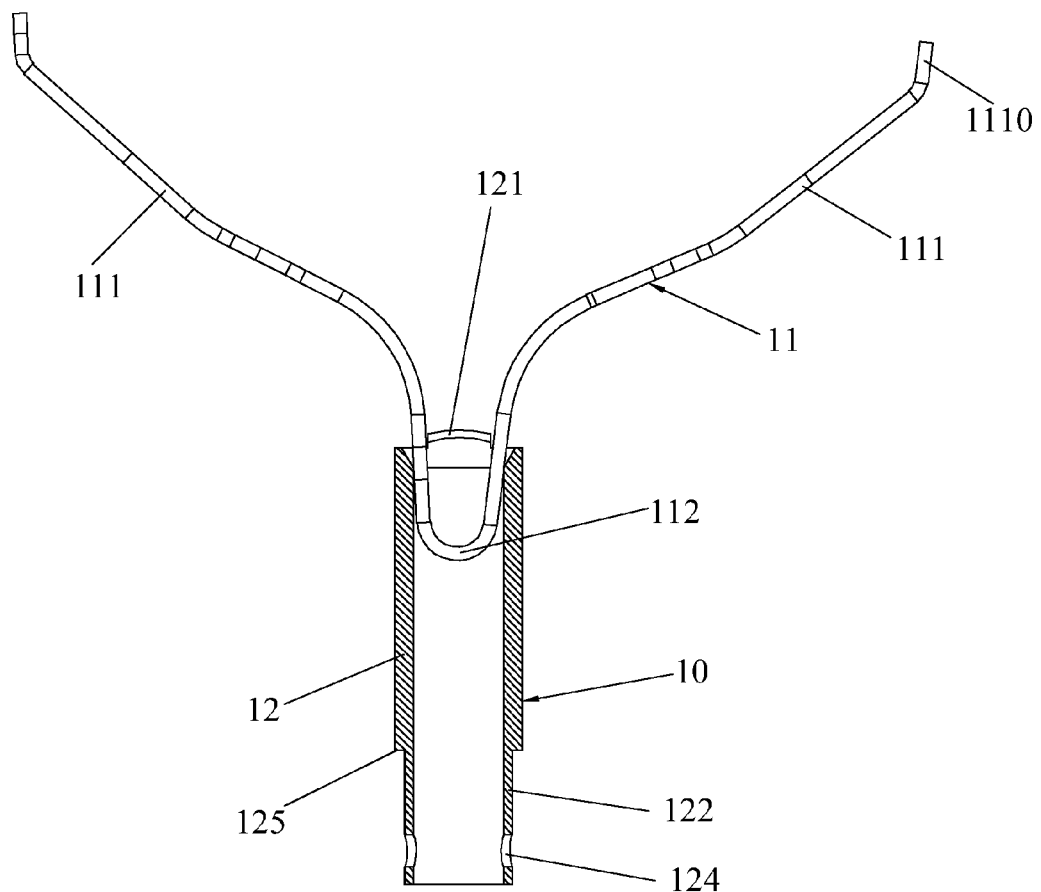
FIG. 5 is a sectional view of the ligation unit shown in FIG. 4.
Figure 19A:
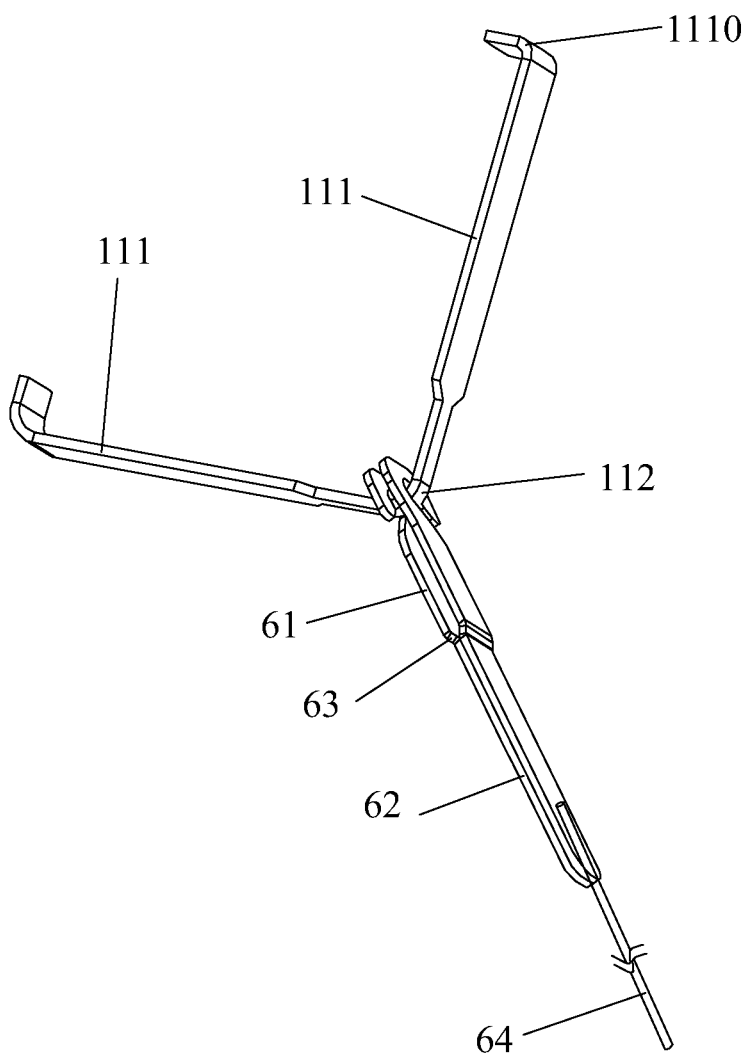
FIGS. 19*a*-19*d* are schematic diagrams showing the traction unit according to another four embodiments of the present invention.

In this embodiment, referring to FIGS. 4 and 5, the ligation component 11 is made by bending a single piece of material, and forms two clamping arms 111 which are plate structure; two clamping arms are connected to each other to form a joint part 112 of the ligation component. In other embodiments, the clamping arms 111 of the ligation component could be plate structure as shown in FIG. 19a, or steel structure shown in FIG. 19b; the plate structure is preferred, because this structure helps in clamping living organisms.

Figure 20:
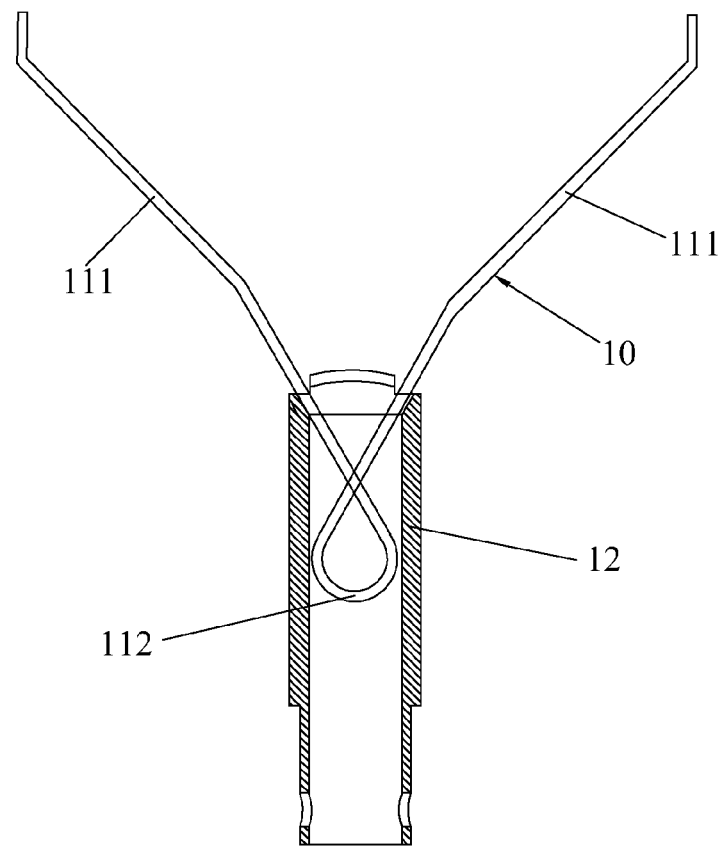
FIGS. 20, 21 and 22 are schematic diagrams showing the ligation unit according to another three embodiments of the present invention.
Figure 21:
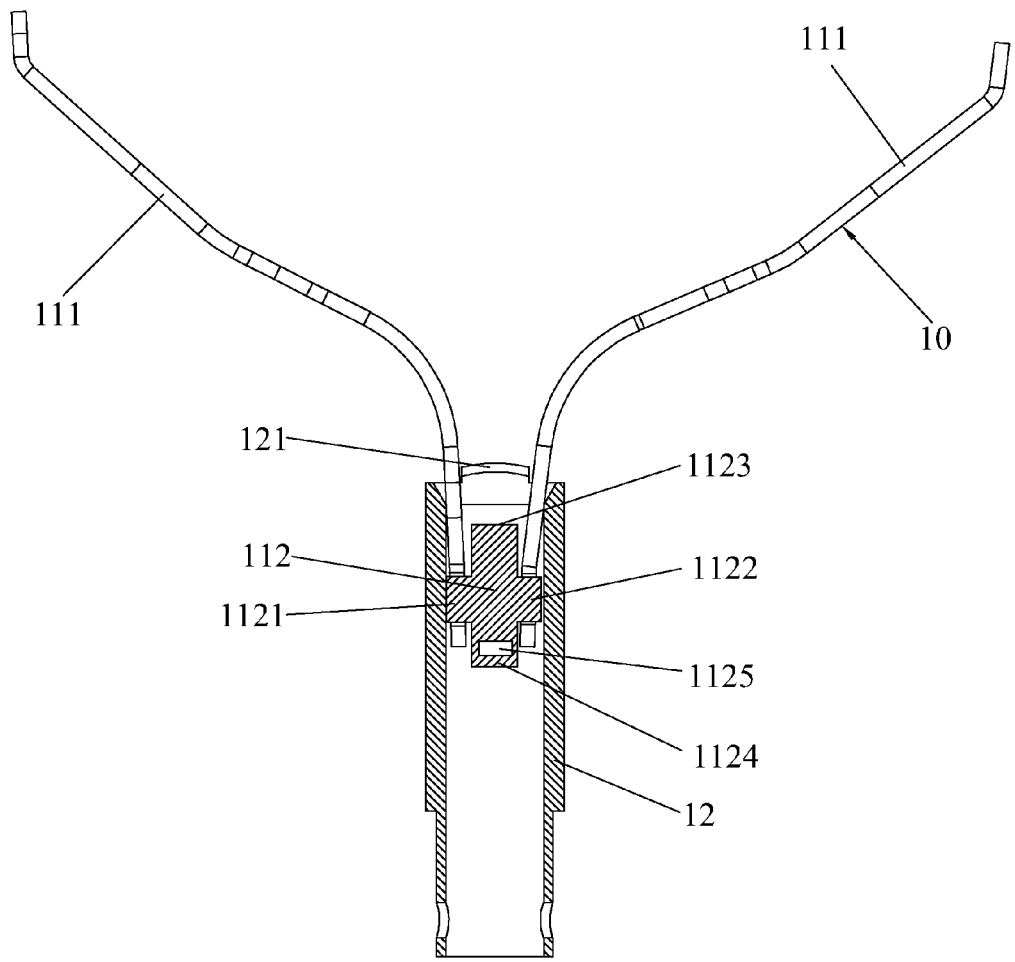
Figure 22:
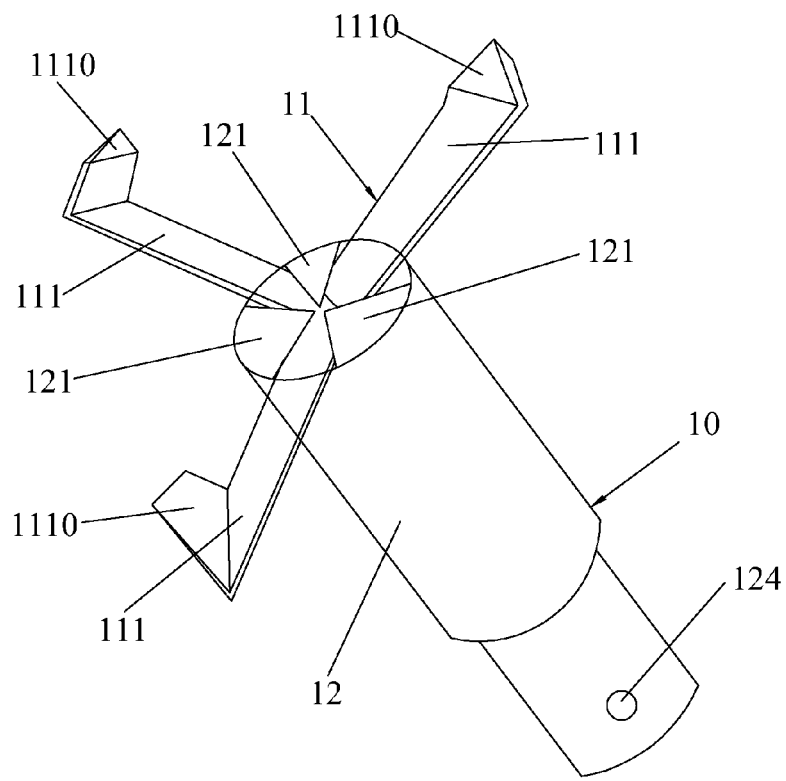

In other embodiments, the ligation component could be other structure. For example, referring to FIG. 20, the ligation component is made by bending a single piece of material into an "8"-shaped structure with two clamping arms 111, and the joint part 112 of the ligation component is a ring. Referring to FIG. 21, the ligation component includes two single clamping arms 111, which are connected to each other by the joint part 112; the joint part 112 includes four parts 1121, 1122, 1123 and 1124 which form a cross-shaped structure, part of the part 1121 faces to the part of the part 1122, and each of them has a mounting hole for mounting the clamping arms 111 thereon; a cutout 1125 is formed in the part 1124 for connecting to the traction unit, and the connecting place is the joint part 112. Referring to FIG. 22, the ligation component includes three clamping arms or more.

The above-mentioned clamping arm has a bending champing head 1110 formed on the top of the clamping arm, which helps in clamping living organisms.

Referring to FIGS. 4 and 5, the accommodation tube 12 is tubular, a separate plate 121 is arranged on the front end 120 (the end near the ligation component) of the accommodation tube 12, for separating the clamping arms 111, and blocking the joint part 112 of the ligation component to limit the extended range of the ligation component, thus the number of the separate plates is the same with the number of the clamping arms. In this embodiment, referring to FIG. 6, the number of the separate plates 121 is two, and the separate plates 121 are alternatively arranged around the end of the accommodation tube at a spacing of 180 degrees, and bent in the direction of the arrow "a" to form the structure shown in FIGS. 4 and 5, so as to separate the clamping arms and blocking the joint part of the ligation component. A chamfer 123 which leans inward is formed on the front end 120 of the accommodation tube 12, and it helps the clamping arms of the ligation component to spread and fold, and serves the function of guiding and supporting. A round step face 122 (with smaller outside diameter of the accommodation tube) is formed in a circumferential direction on the back end of the accommodation tube 12, a step 125 is formed by the step face 122 and the other part of the accommodation tube, and a connector 124 is formed on the step face 122. The connector 124 is a hole according to this embodiment, and the connector 124 could be slot in other embodiments, the connector 124 is corresponding to a connector 222 of a sleeve disclosed below and a bent portion 410 of the connecting unit.

In other embodiments of the present invention, the accommodation tube could be other structure. For example, referring to FIG. 22, the accommodation tube has three separate plates 121 to correspond to three clamping arms, and each of three separate plates 121 is like a triangle.

Figure 23:
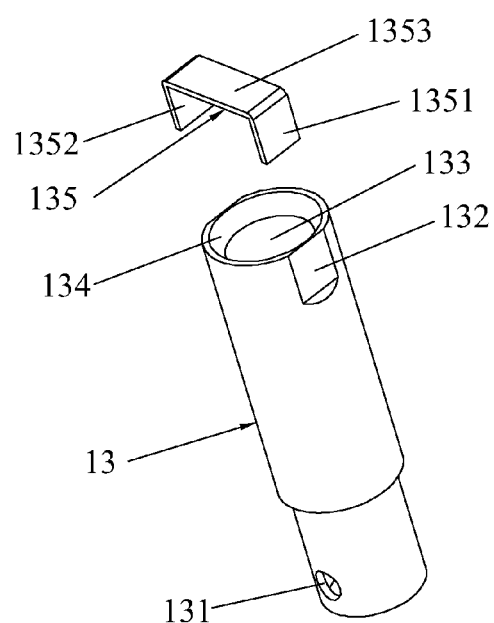
FIGS. 23, 24 and 25 are schematic diagrams showing the accommodation tube of the ligation unit according to another three embodiments of the present invention.

Referring to FIG. 23, the structure of the back end of the accommodation tube 13 is identical with that of the accommodation tube disclosed in the above embodiment, which has a step face and a connecting hole 131. The separate plate 135 has two vertical portion 1351 and 1352, which are connected by a horizontal portion 1353; two vertical portion 1351 and 1352 are connected to the copula 132 formed on the front end 133 of the accommodation tube. Likewise, a chamfer 134 is formed on the opening of the front end 133 of the accommodation tube 13.

Figure 24:
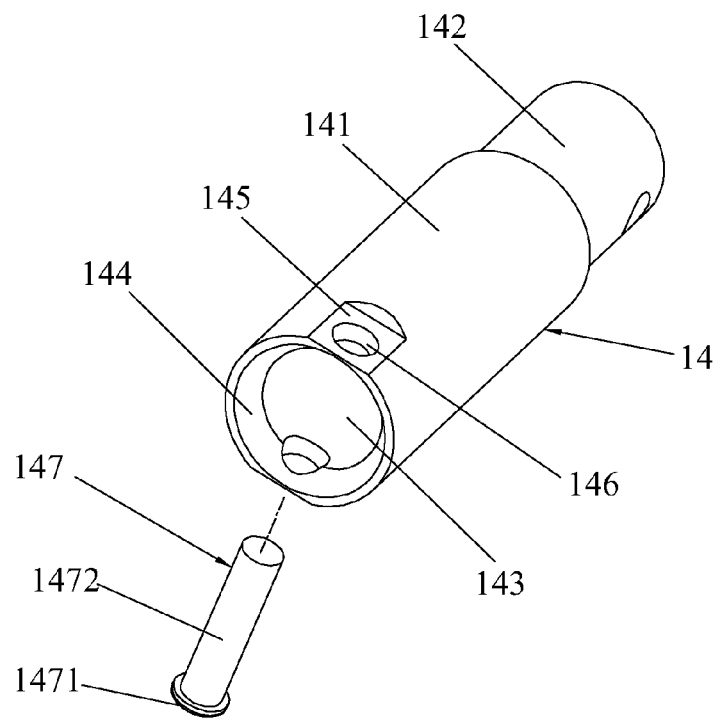

Referring to FIG. 24, the structure of the back end 142 of the accommodation tube 14 is identical with that of the accommodation tube disclosed in the above embodiment, which has a step face 142 and a connecting hole. But the separate plate 147 is a pin and has a pin body 1472 and a pin head 1471; a mounting hole 146 is formed on the front end 143 of the accommodation tube 14 for the separate plate 147 to run through, and the front end of the tube wall 141 is provided with a stand 145. A chamfer 144 is formed on the opening of the front end 143.

Figure 6:
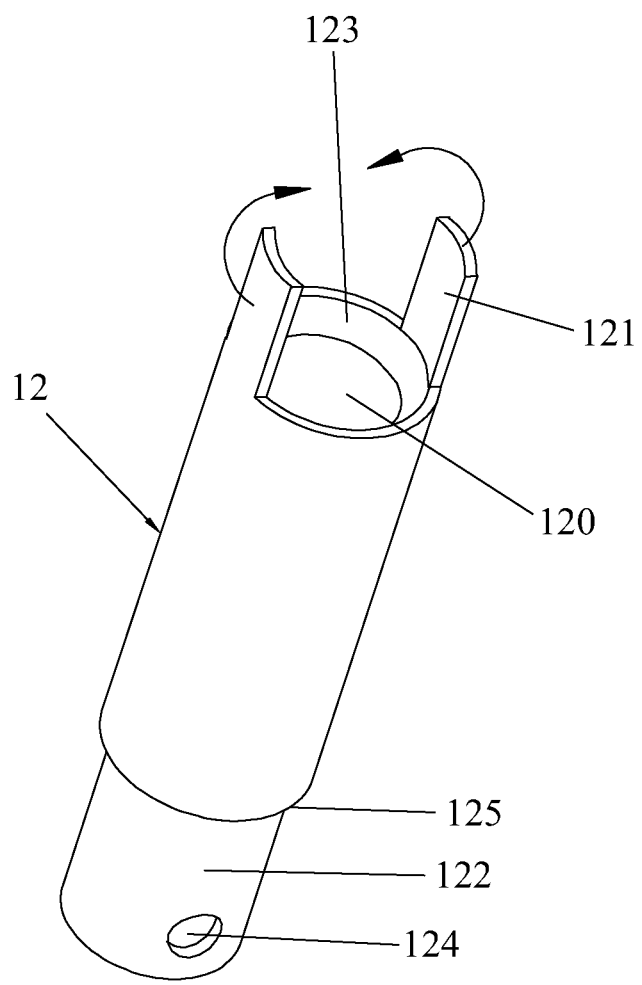
FIG. 6 is a schematic diagram of an accommodation tube of the ligation unit shown in FIG. 4.
Figure 25:
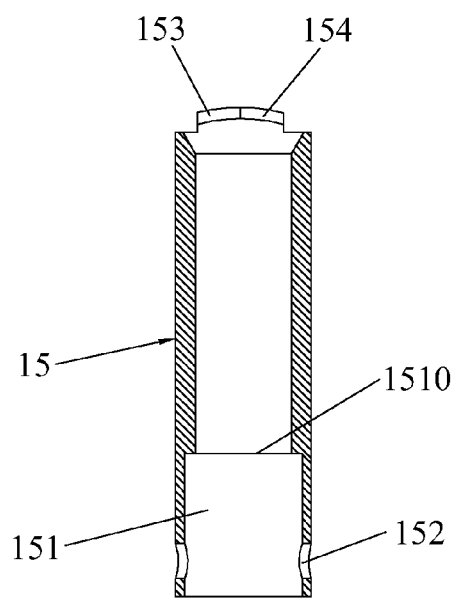

Referring to FIG. 25, a step hole 151 (whose aperture is larger than that of other holes formed on the front end of the accommodation tube 15) is formed on the back end of the accommodation tube 15, the step hole 151 combined with the narrow hole above forms a step 1510, and a connecting hole 152 is formed on the wall of the step hole 151; two separate plates 153 and 154 are arranged on the front end of the accommodation tube 15, which have structures similar to those of the separate plates shown in the embodiment shown in FIG. 6.

According to the above embodiments, the front end of the accommodation tube is matched with the ligation component, and the back end of the accommodation tube is matched with the sleeve of the conveying unit.

Conveying Unit

Referring to FIGS. 2, 3, 7 and 8, a conveying unit 20 is connected to the back end of the accommodation tube along their vertical direction, and the conveying unit 20 includes a flexible tube 21 and a sleeve 22 which is mounted on the front end of the flexible tube.

In the embodiment, the flexible tube 21 is made by flat steel wires by enwinding to obtain as large a chamber as possible, and is capable of withstanding longitudinal forces and achieving bending to some degree. In this embodiment, the flexible tube 21 also could be made by round steel wires by enwinding; or the flexible tube 21 could be made by some different steel wires; or the flexible tube 21 is made of woven wire net, or made of composites composed of woven wire net and plastic. The sleeve 22 is mounted to the front end of the flexible tube 21 by welding.

The front end of the sleeve 22 is engaged with the accommodation tube 12 to form a junction, where a wall of the sleeve 22 is overlapped a wall of the accommodation tube 12; one respective wall of the sleeve and the accommodation tube has a connection hole formed at the junction to be corresponding to each other, for the bent portion of the connecting unit to lock in (detailed disclosure is as follow).

Figure 7:
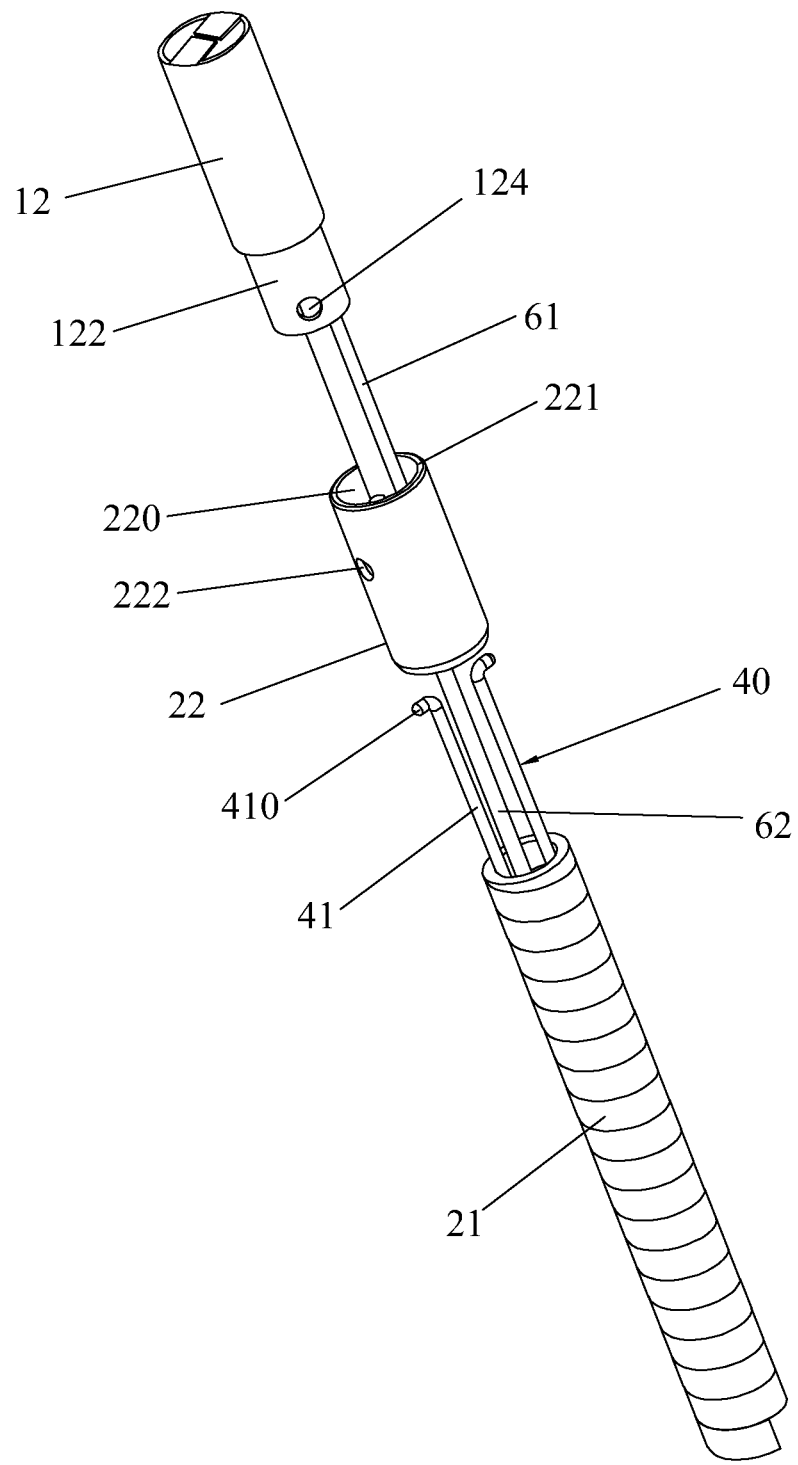
FIG. 7 is an partial explode diagram of the clamping and ligation device shown in FIG. 1, showing the accommodation tube, a sleeve and a flexible tube of the conveying unit, the connecting unit and the traction unit.
Figure 8:
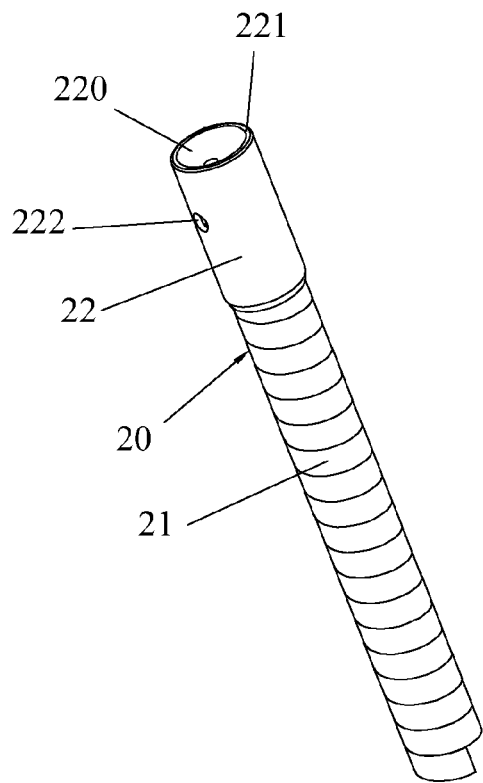
FIG. 8 is a schematic diagram of the connecting unit shown in FIG. 1.
Figure 9:
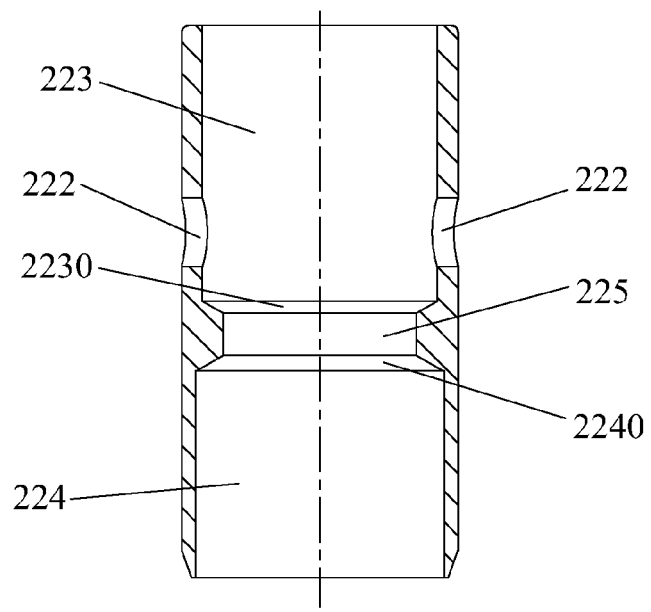
FIG. 9 is a sectional view of the sleeve of the conveying unit shown in FIG. 8.

Referring to FIGS. 6 and 7, as said above, a step face 122 (the surface with smaller outside diameter of the accommodation tube) is formed on the back end of the accommodation tube 12. Preferably, in this embodiment, referring to FIG. 9, the sleeve 22 has a stepped hole (including an upper hole 223, a lower hole 224 and a middle hole 225 to form stepped structure), the upper hole 223 is matched with the step face 122 of the accommodation tube 12, that is, a portion of the accommodation tube 12 which has a small outside diameter inserts into the upper hole 223, the step 2230 formed by the upper hole 223 and the middle hole 225 is abutted against the step face (the back end of the accommodation tube) of the accommodation tube 12, and the step 125 formed on the accommodation tube 12 is abutted against the end of the upper hole 223. Accordingly, the wall of the sleeve 22 is overlapped the wall of the accommodation tube 12; a connecting hole 222 is formed on the wall of the upper hole 223; the connecting hole 222 is communicated with the connecting hole 124 of the accommodation tube 12. The lower hole 224 is matched with the front end of the accommodation tube 12, the front end of the accommodation tube 12 inserts into the lower end 124 and mounted therein by welding, and the front end of the accommodation tube 12 is abutted against the step 2240 formed by the lower hole 224 an the middle hole 225.

Figure 28:
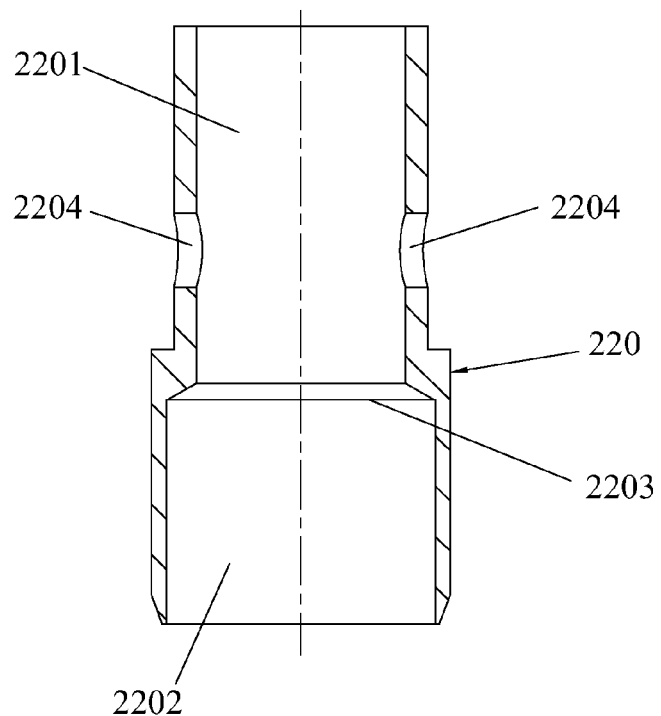
FIG. 28 is a schematic diagram showing the sleeve of the conveying unit according to another embodiment of the present invention.

In other embodiments of the present invention, the sleeve could be other structures. For example, referring to FIG. 28, the sleeve 220 has a stepped hole (the upper hole 2201 and lower hole 2202 to form a step structure), the upper hole 2201 is matched with the step face 122 of the accommodation tube, and the lower hole 2202 is matched with the flexible tube 21. The step 2203 formed by the upper hole 2201 and the lower hole 2202 is abutted against the step face of the accommodation tube 12, and the step 125 formed on the accommodation tube 12 is abutted against the end of the upper hole 2201. Accordingly, the wall of the sleeve 220 is overlapped the wall of the accommodation tube 12; a connecting hole 2204 is formed on the wall of the upper hole 2201, and the connecting hole 2204 is communicated with the connecting hole 124 of the accommodation tube 12. Likewise, the step 2203 is abutted against the end of the flexible tube 21, and the wall of the flexible tube 21 is mounted in the lower hole 2202 by welding.

In other embodiments of the present invention, referring to FIG. 25, a stepped hole 151 is formed on the back end of the accommodation tube, and a connecting hole 152 is formed on the wall of the stepped hole 151; accordingly, the sleeve has a corresponding step face.

In above embodiments, the accommodation tube is matched with the sleeve, by using the principle that "a boss is matched with a stepped hole". Thus, only if the abutment and the overlapping of two walls are achieved, any technique could be used in the present invention.

Protective Sleeve

A protective sleeve 30 is sleeved outside the conveying unit 20 and the ligation unit 10, and the conveying unit 20 and the ligation unit 10 could moved lengthwise in the protective sleeve, that is, the inside diameter of the protective sleeve 30 is larger than the outside diameters of the conveying unit 20 and the ligation unit 10. Referring to FIGS. 1 and 2, during the process of ligation, the whole ligation unit and the front end of the conveying unit are both pushed outside the protective sleeve. Referring to FIG. 3, the ligation unit is accommodated completely in the protective sleeve owing to the length of the protective sleeve, and the ligation component would not extend outward from the protective sleeve; thus, when the ligation unit runs through the channel of the endoscope, the protective sleeve could avoid the damage of the ligation component of the ligation unit or the ligation component being stuck in the endoscope. In this embodiment, referring to FIGS. 1, 12, 13 and 14, a handle is arranged on the back end of the protective sleeve, for holding to push and pull the protective sleeve.

Figure 13:
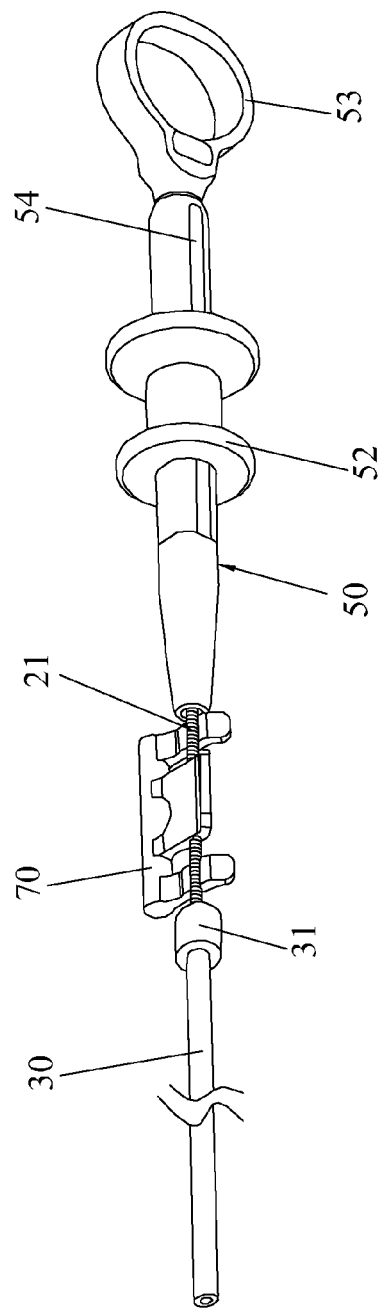
FIG. 13 is a stereogram of the clamping and ligation device shown in FIG. 1, with the stopper unit being mounting on the flexible tube, and the ligation unit being contained in the protective sleeve.

In the embodiment, as shown in FIG. 13, the protective sleeve has only one channel, and the conveying unit 20 and the ligation unit 10 run through the channel.

Figure 26:
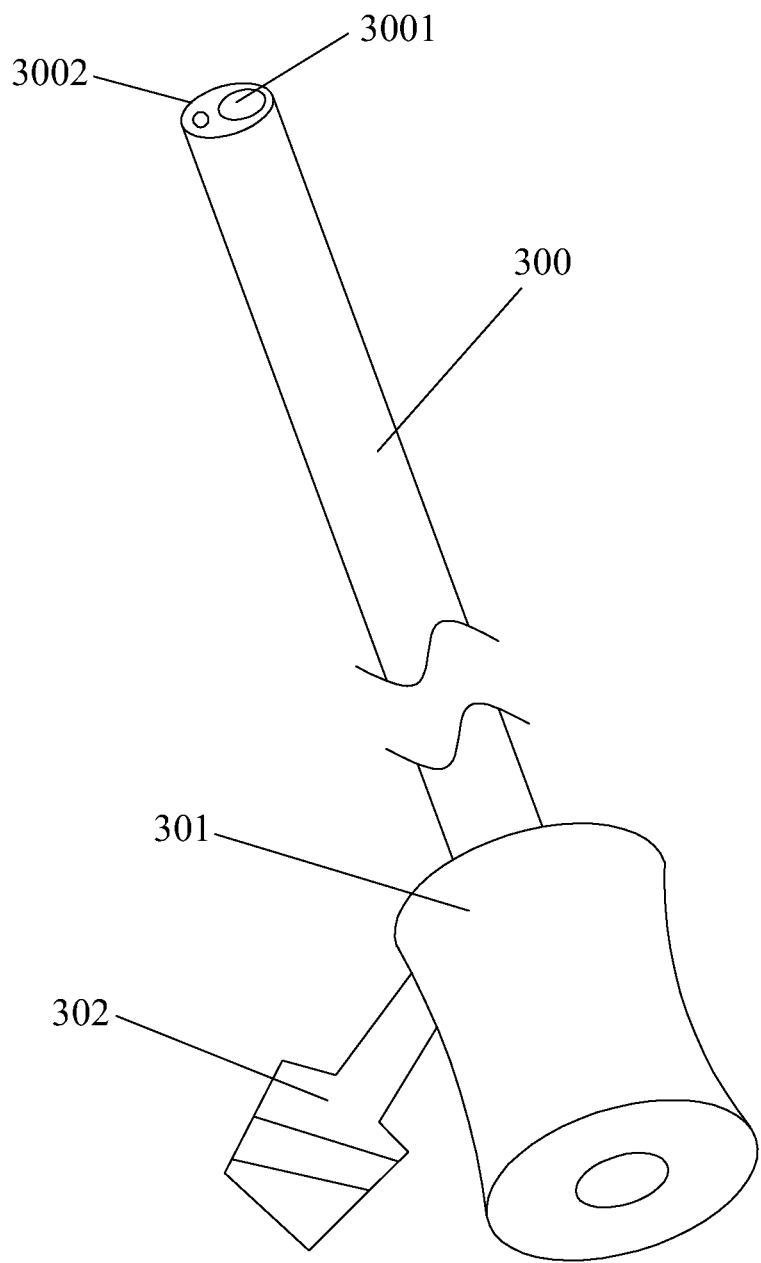
FIGS. 26 and 27 are schematic diagrams showing the protective sleeve according to another two embodiments of the present invention.

Preferably, in another embodiment of the present invention, referring to FIG. 26, the protective sleeve 300 includes two channels 3001 and 3002, and the conveying unit and the ligation unit run through the channel 3001, the channel 3002 is used for transporting liquid and gas used in the operation, in this embodiment, a handle 301 is mounted on the back end of the protective sleeve 300, and a operating rod 302 is mounted on the handle 301 for pushing and pulling the protective sleeve.

Figure 27:
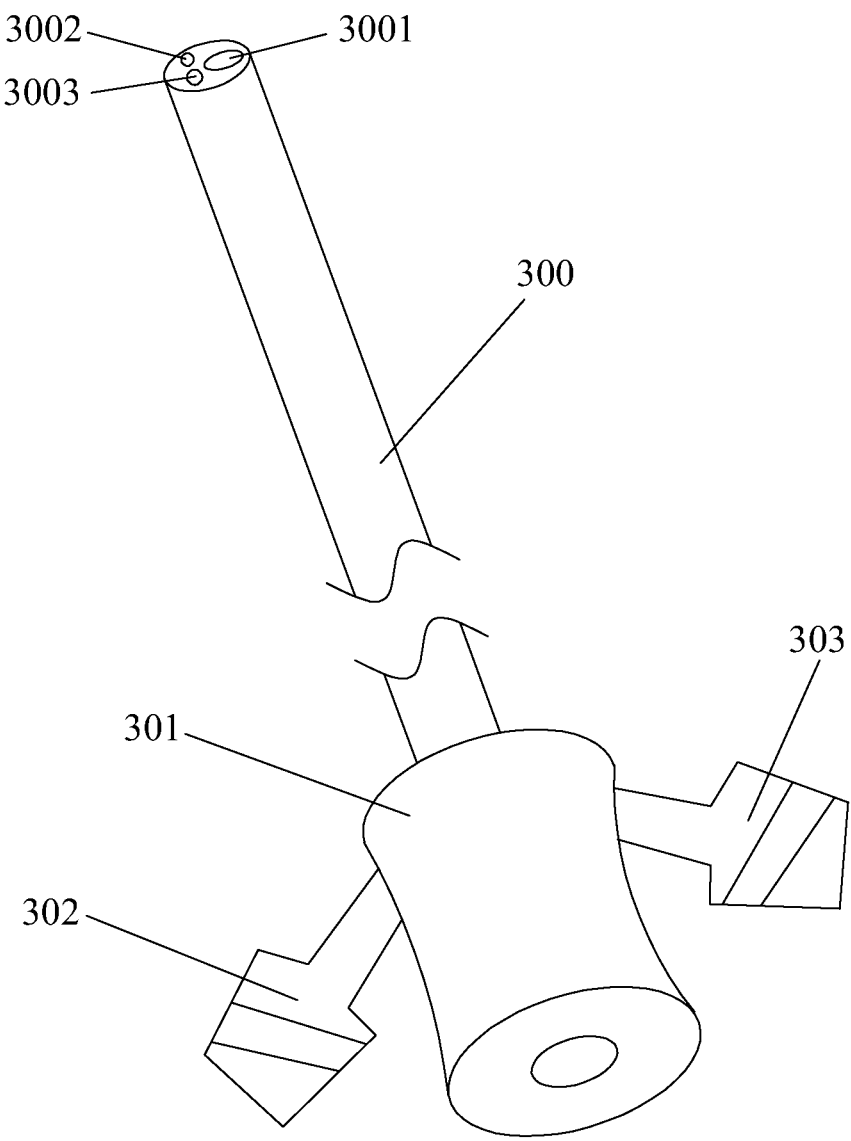

Preferably, in another embodiment of the present invention, referring to FIG. 27, the protective sleeve 300 includes three channels 3001, 3002 and 3003, and the conveying unit and the ligation unit run through the channel 3001, the channels 3002 and 3003 are used for transporting other material. In this embodiment, a handle 301 is mounted on the back end of the protective sleeve, and two operating rods 302 and 303 are mounted on the handle 301.

In the above embodiments of the present invention, the protective sleeves are all flexible, and preferably made of PE, PVC or PP material, as soft sleeves. Other sleeves which are capable of bending also could be used in the present invention. Accordingly, the clamping and ligation device inserts into the body with flexible structure, for ease of the operation and protecting the living organisms in the body.

Connecting Unit

Referring to FIGS. 1, 2, 3 and 11, a connecting unit 40 is made by bending a single piece of material, and includes two legs 41, whose bottom ends are coupled to form a contact portion 42, the top end of each leg 41 has a bent portion 410, and the bent portion 410 inserts into the connection hole 222 formed on the conveying unit and the connection hole 124 formed on the accommodation tube 12, so as to connect the conveying unit 20 and the accommodation tube 12 together. When the leg 41 is under longitudinal force (that is the contact portion 42 is under longitudinal force), the bent portion 410 could deform (e.g. straighten) and is disengaged from the connection hole 222 of the conveying unit and the connection hole 124 of the accommodation tube 12, so that the conveying unit 20 is separate from the accommodation tube 12 (ligation unit). Preferably, the connecting unit 40 is made by bending a single steel sheet or steel rebar, or other material.

In other embodiments of the present invention, the connecting unit could be other structures, the number of the leg could be one or more than three, and not every leg has bent portion.

Figure 29:
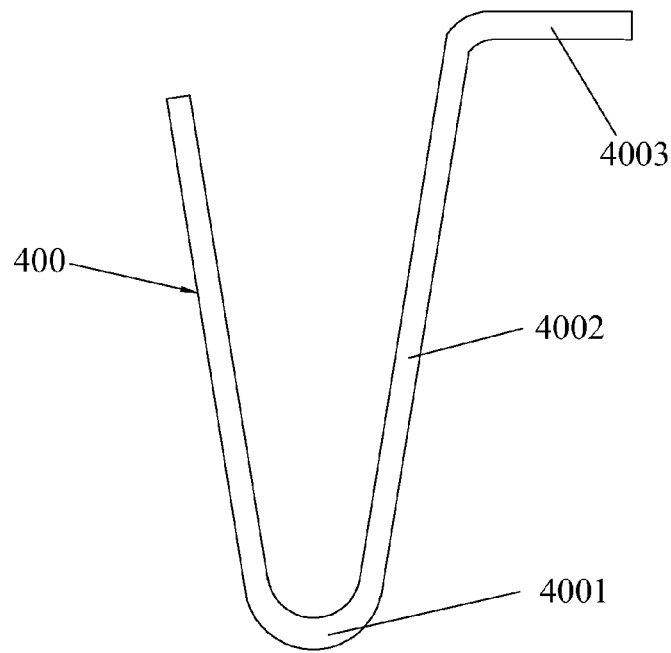
FIGS. 29-35 are schematic diagrams showing the connecting unit according to another seven embodiments of the present invention.

Referring to FIG. 29, the connecting unit 400 is a V-shaped structure made by bending a single material, and it includes a left leg and a right leg, two legs are coupled to each other to form a contact portion 4001, only the leg 4002 has a bent portion 4003 formed on the top end of the leg 4002, and the bent portion 4003 could insert into the respective connection hole formed on the conveying unit 20 and the accommodation tube 12, of course, each of the conveying unit and the accommodation tube has a corresponding connecting hole.

Figure 30:
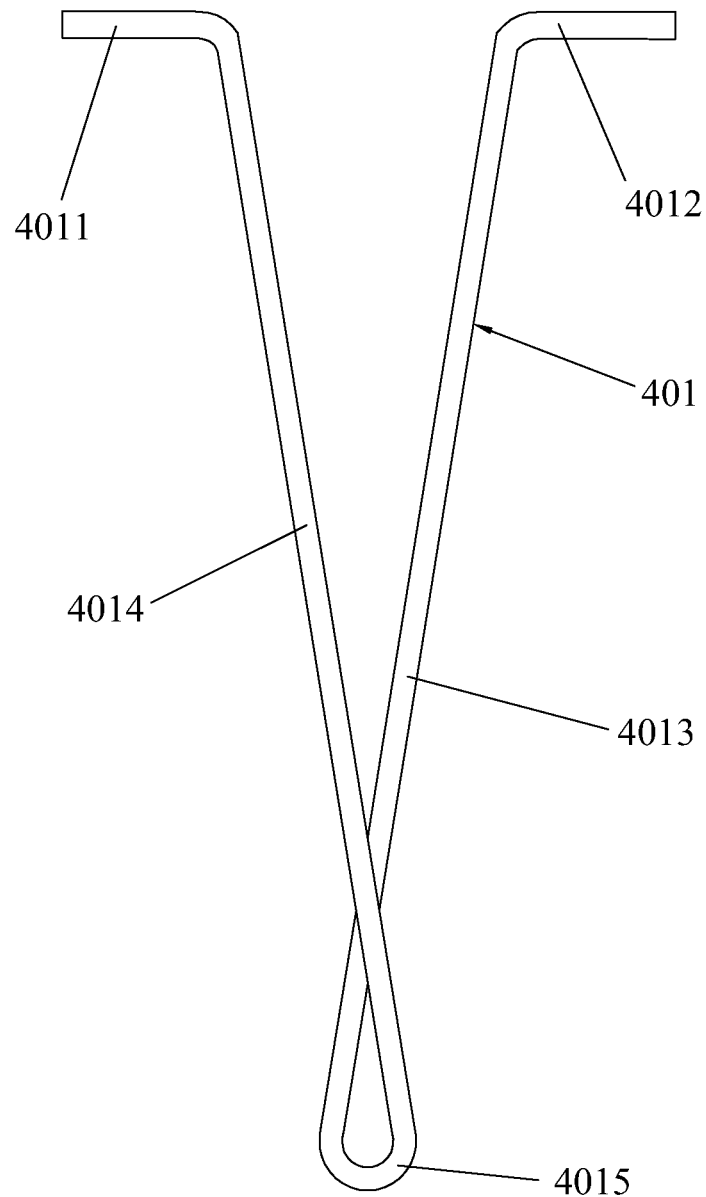

Referring to FIG. 30, the connecting unit 401 is an "8"-shaped structure made by bending a single material, and it includes a left leg 4014 and a right leg 4013, the two legs are coupled to each other to form a contact portion 4015 with circular shape, the bent portion 4011 and the bent portion 4012 are respectively formed on the top ends of two legs, and could insert into the respective connection hole formed on the conveying unit and the accommodation tube.

Figure 31:
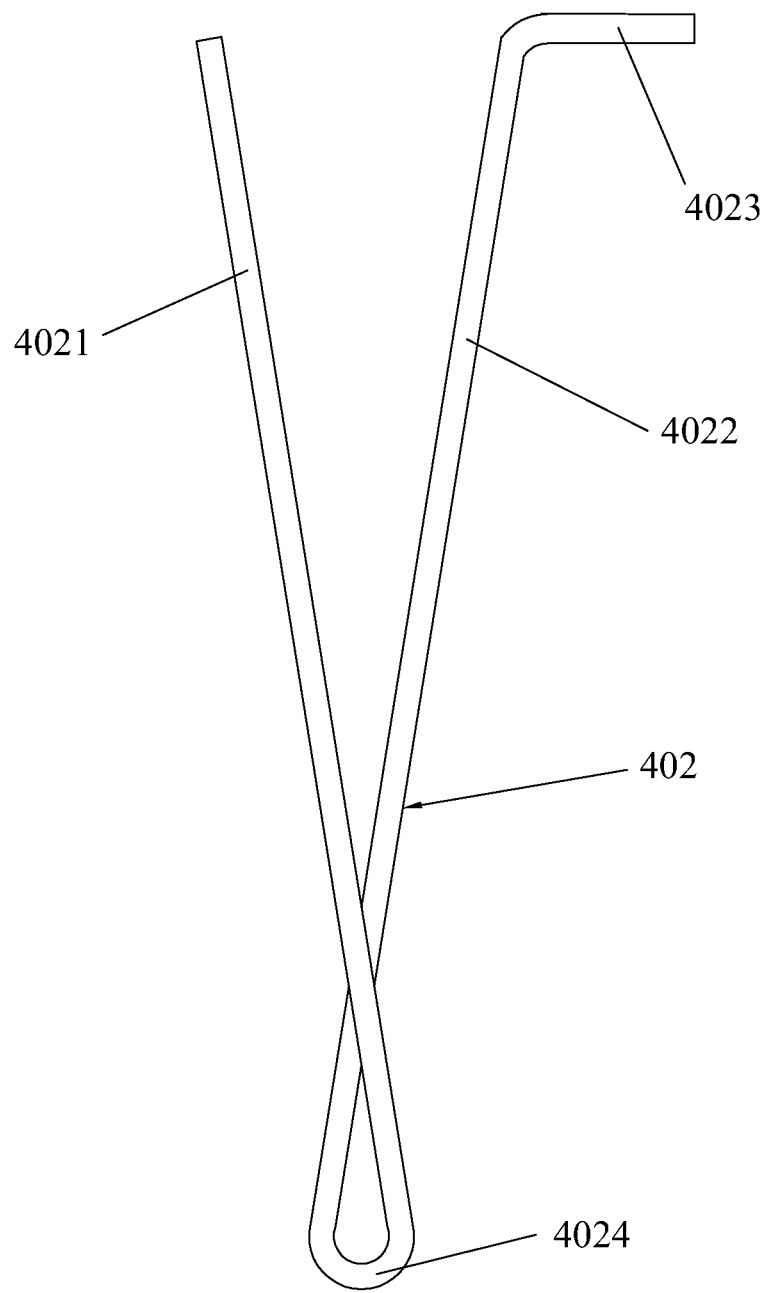

Referring to FIG. 31, the structure of the connecting unit 402 is similar to that of the connecting unit 401 shown in FIG. 30, the connecting unit 40 also includes a left leg 4021 and a right leg 4022, and the two legs are coupled to each other to form a contact portion 4024 with circular shape, the difference is: only the right leg 4022 of the connecting unit 402 has a bent portion 4023 formed on the top end thereof, the left leg 4021 does not has a bent portion. Correspondingly, each of the conveying unit and the accommodation tube has only one connecting hole.

Figure 32:
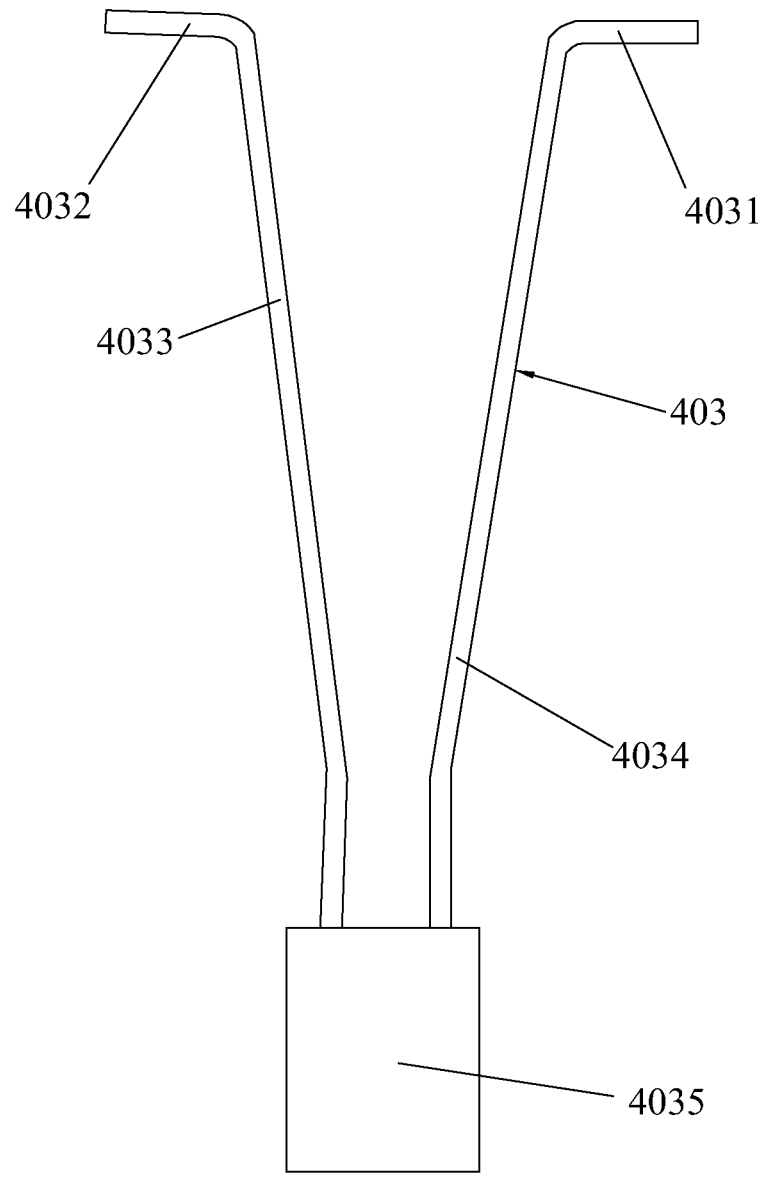

Referring to FIG. 32, the connecting unit 403 includes two legs 4033 and 4034, and the connecting unit 403 is not made by bending a single material, but made by two single legs 4033 and 4034. The contact portion 4035 is connected to the bottom ends of two legs. The bent portion 4032 and the bent portion 4031 are respectively formed on the top ends of two legs 4033 and 4034.

Figure 33:
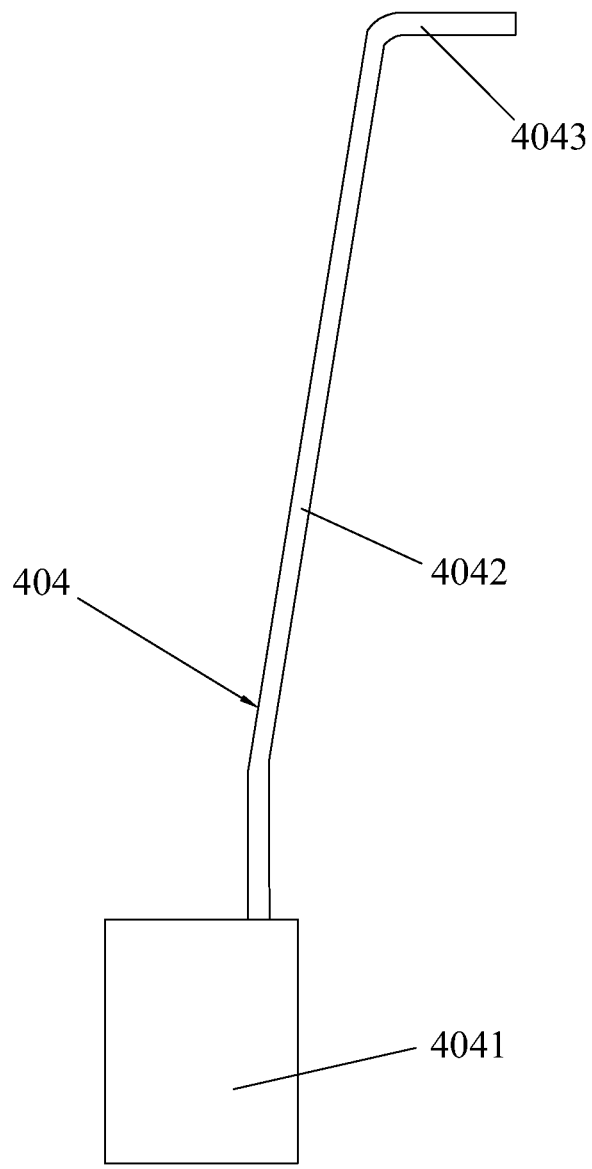

Referring to FIG. 33, the structure of the connecting unit 404 is similar to that of the connecting unit 403 shown in FIG. 32, the difference is that the connecting unit 404 only has a leg 4042, whose top end is provided with a bent portion 4043, and the back end is provided with a contact portion 4041. Correspondingly, each of the conveying unit and the accommodation tube has only one connecting hole.

Figure 34:
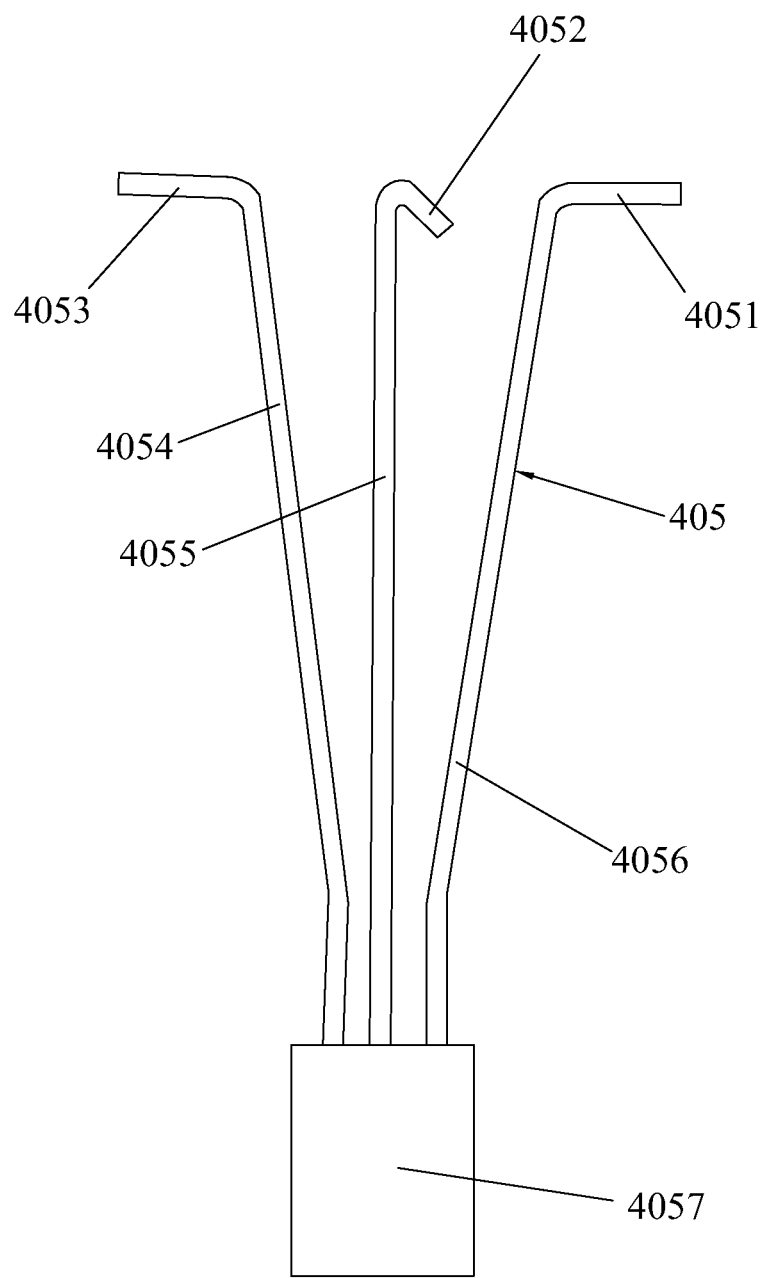

Referring to FIG. 34, the structure of the connecting unit 405 is similar to that of the connecting unit 403 shown in FIG. 32, but the connecting unit 405 has three legs 4054, 4055 and 4056, each top end of the three legs has bent portion 4053, 4052 and 4051, and a contact portion 4057 is arranged on each bottom end of three legs.

Figure 35:
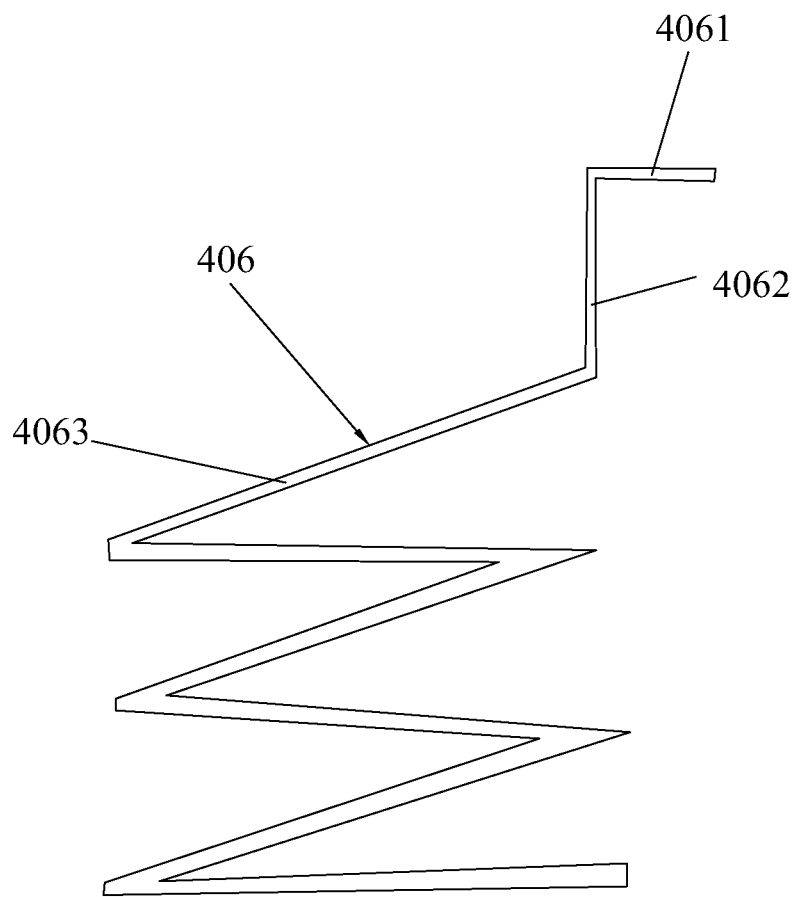

Referring to FIG. 35, the connecting unit 406 includes two legs, one leg 4063 is serrated structure, and the top end of it is without a bend portion, the other leg 4062 is vertically connected to the top end of the leg 4063, the top end of the leg 4062 has a bent portion 4061 to connect to the conveying unit and the accommodation tube.

The connecting unit could be any other suitable structure in the prior art.

Operation Unit

Figure 14:
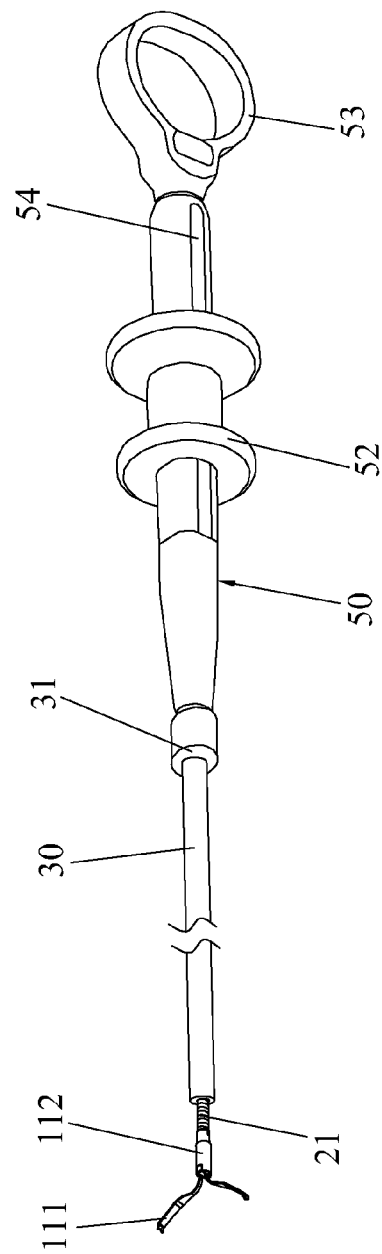
FIG. 14 is a stereogram of the clamping and ligation device shown in FIG. 1 without the stopper unit, with the ligation unit being pushed outside the protective sleeve.
Figure 15:
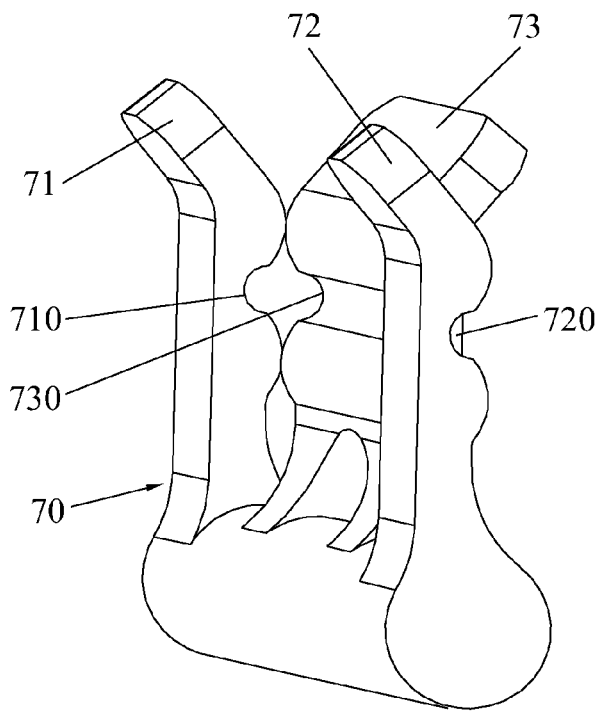
FIG. 15 is a stereogram of the stopper unit shown in FIG. 13.

Referring to FIGS. 1, 13 and 14, an operation unit 50 includes an operation rod 51 and an operation block 52 controlling the movement of the operation rod 51, a main body 54, and a handle 53 arranged on the back end of the main body 54. The back end of the flexible tube 21 of the conveying unit 20 is mounted on the front end of the main body 54 of the operation unit 50, so that the conveying unit 20 is connected to the main body 54 of the operation unit 50.

The operation rod 51 runs through the main body 54 and could move lengthwise in the main body 54, the front end of the operation rod 51 is connected to the back end of the traction unit 60 (which is disclosed as follow and shown in FIG. 10), the back end of the operation rod 51 is connected to the operation block 52. A sliding chute 540 is formed on the main body 54, the operation block 52 is mounted on the main body 54 and guided by the sliding chute 540, the operation block 52 is pushed or pulled to pull the operation rod 51 to move forward or backward, so that the traction unit 60 is made to move in the conveying unit 20 forward or backward.

In other embodiments of the present invention, the operation unit could be any other suitable structure in the prior art.

Preferably, referring to FIGS. 1 and 13, the clamping and ligation device further includes a stopper unit 70, which is removably mounted on the back end of the flexible tube 21 of the conveying unit 20, and the mounting place is the junction of the flexible tube 21 and the operation unit 50. Thus, the protective sleeve 30 (and the handle 301) could move forward driven by the stopper unit 70, the ligation unit 10 and the conveying unit 20 are therefore move into the protective sleeve 30, so as to achieve that the protective sleeve 30 contains and protects the ligation unit 10, and the position is limited; the clamping and ligation device would not damage and get stuck in the endoscope when passing through the endoscope, and does not need a large push. Referring to FIG. 14, after the clamping and ligation passes through the endoscope, the stopper unit 70 is fetched out from the flexible tube 21 to make the protective sleeve 30 move back, so that the ligation unit 10 (and the conveying unit 20) move outside the protective sleeve.

Figure 18:
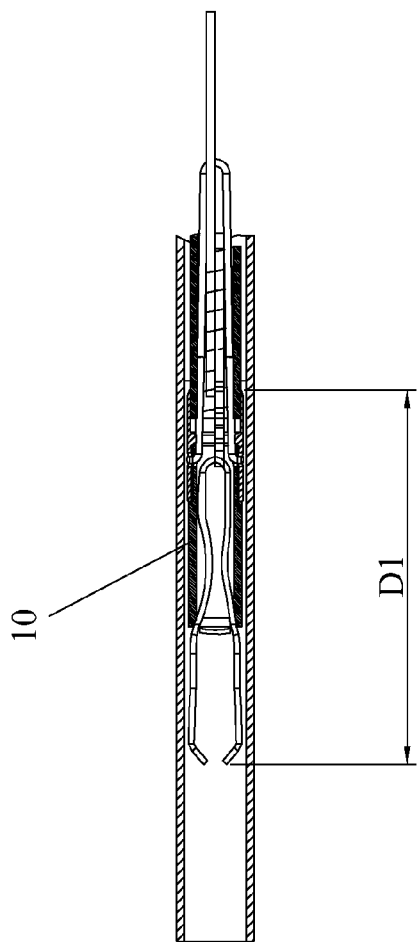
FIG. 18 is a front view of the stopper unit shown in FIG. 15 and a partial schematic diagram of the clamping and ligation device shown in FIG. 1, showing the relationship of the lengths of the stopper and the ligation unit.
Figure 18:
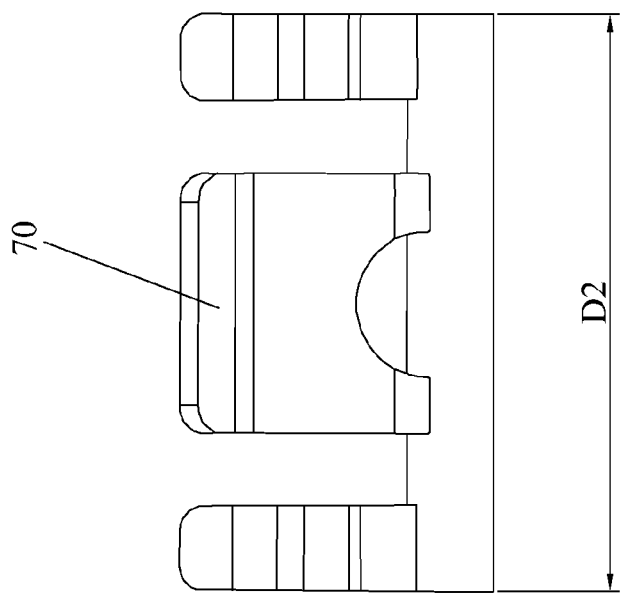

In order to make the ligation unit to contain in the protective sleeve 30 completely after the ligation component is folded, as shown in FIG. 18, the length D2 of the stopper unit 70 (in the vertical direction of the flexible tube 21) is greater than the length D1 of the whole ligation unit 10 in the vertical direction when the ligation component is folded.

Figure 16:
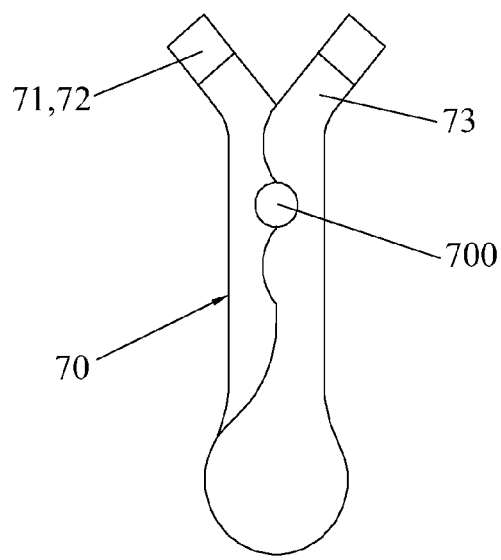
FIG. 16 is a side view of the stopper unit shown in FIG. 15.

As a prefer embodiment, referring to FIGS. 13, 15, 16, 17a and 17b, the stopper unit 70 includes three flexible stopper arms 71, 73 and 72 which are arranged in row and coupled to each other at the bottom, the flexible stopper arms 71 and 72 could move in the same direction, and the flexible stopper arm 73 moves in the opposite direction to stopper arms 71 and 72. Limit recesses 710 and 720 are respectively formed on the flexible stopper arms 71 and 72 to match with the flexible tube 21, and the limit recess 730 is formed on the flexible stopper arm 73 to match with the flexible tube 21. Referring to FIG. 16, as shown in this side view, the limit recesses 710, 720 and 730 form a limit hole 700, for limiting the position of the flexible tube 21.

Figure 17A:
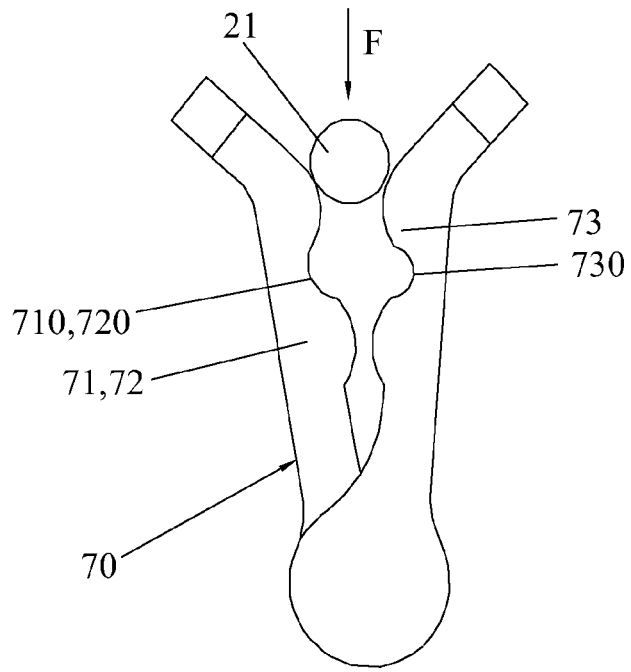
FIG. 17*a* is a side view of the stopper unit shown in FIG. 15, showing the process of the stopper unit being mounted on the flexible tube.
Figure 17B:
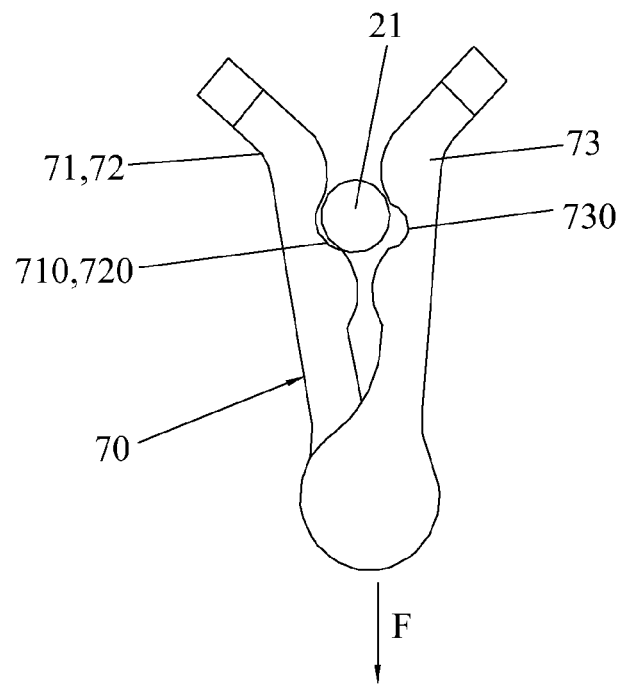
FIG. 17*b* is a side view of the stopper unit shown in FIG. 15, showing the process of the stopper unit being taken away from the flexible tube.

FIG. 17a demonstrates the process of the stopper unit 70 being mounted on the flexible tube 21. The flexible stopper arms 71, 73 and 72 are separated, and the flexible tube 21 is pressed along the direction of arrow F, to insert into the limit hole 700 formed by the limit recesses 710, 720 and 730, so the installation is achieved. FIG. 17b demonstrates the process of the stopper unit 70 being taken away from the flexible tube 21, and the flexible tube 21 is fetched out from the limit hole 700 along the direction opposite to the arrow F.

According to another embodiment of the present invention, the stopper unit includes merely two flexible stopper arms, that is, reducing one of the flexible stopper arms 71 and 72 in the above embodiment, but the stability of locking the flexible tube 21 may not be that good as shown in the above embodiment. Of course, in another embodiment, the stopper unit includes three flexible stopper arms, some of the flexible stopper arms move in a certain direction, and the remaining the flexible stopper arms move in the opposite direction (each two adjacent flexible stopper arms are moved in the opposite direction), one limit recess is formed on each of the flexible the stopper arms for locking the flexible tube, all limit recesses form a limit hole. The stopper unit could be any other suitable structure in the prior art.

Traction Unit

Figure 10:
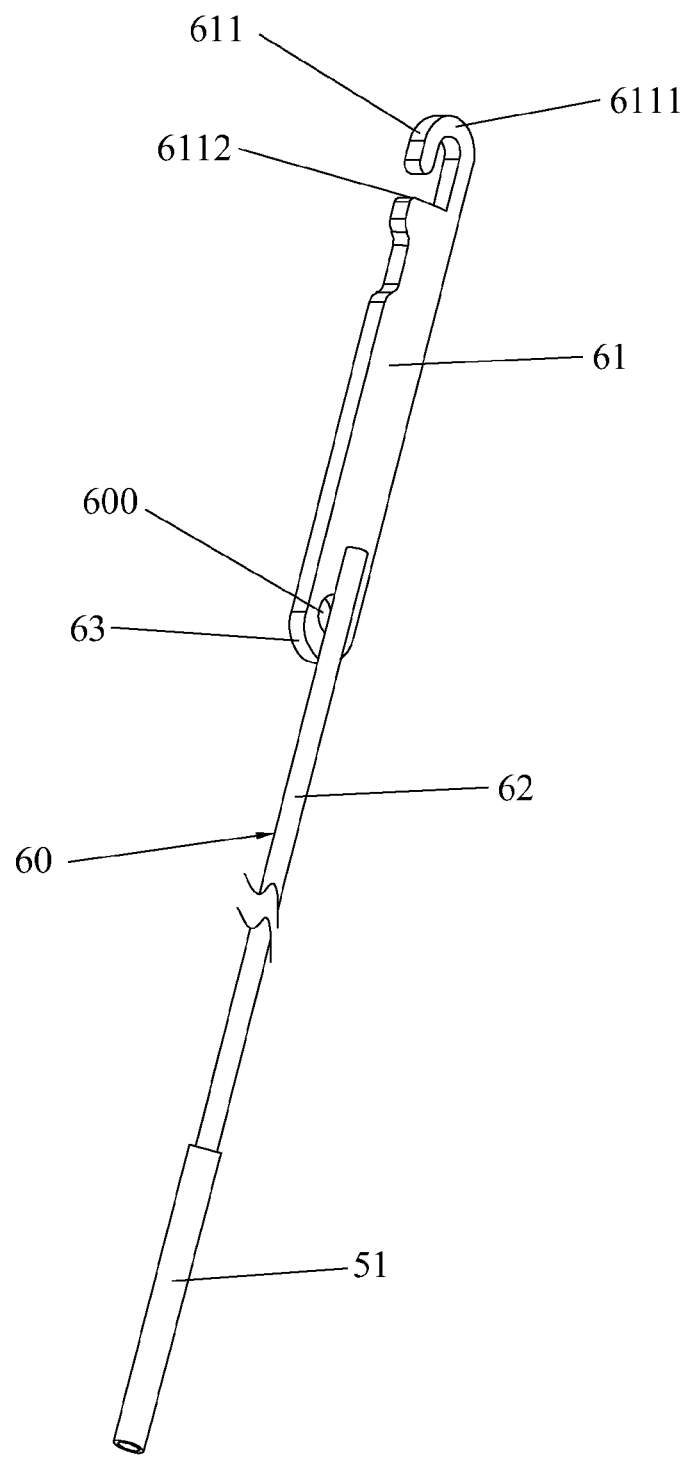
FIG. 10 is a schematic diagram of the traction unit of the clamping and ligation device shown in FIG. 1.
Figure 11:
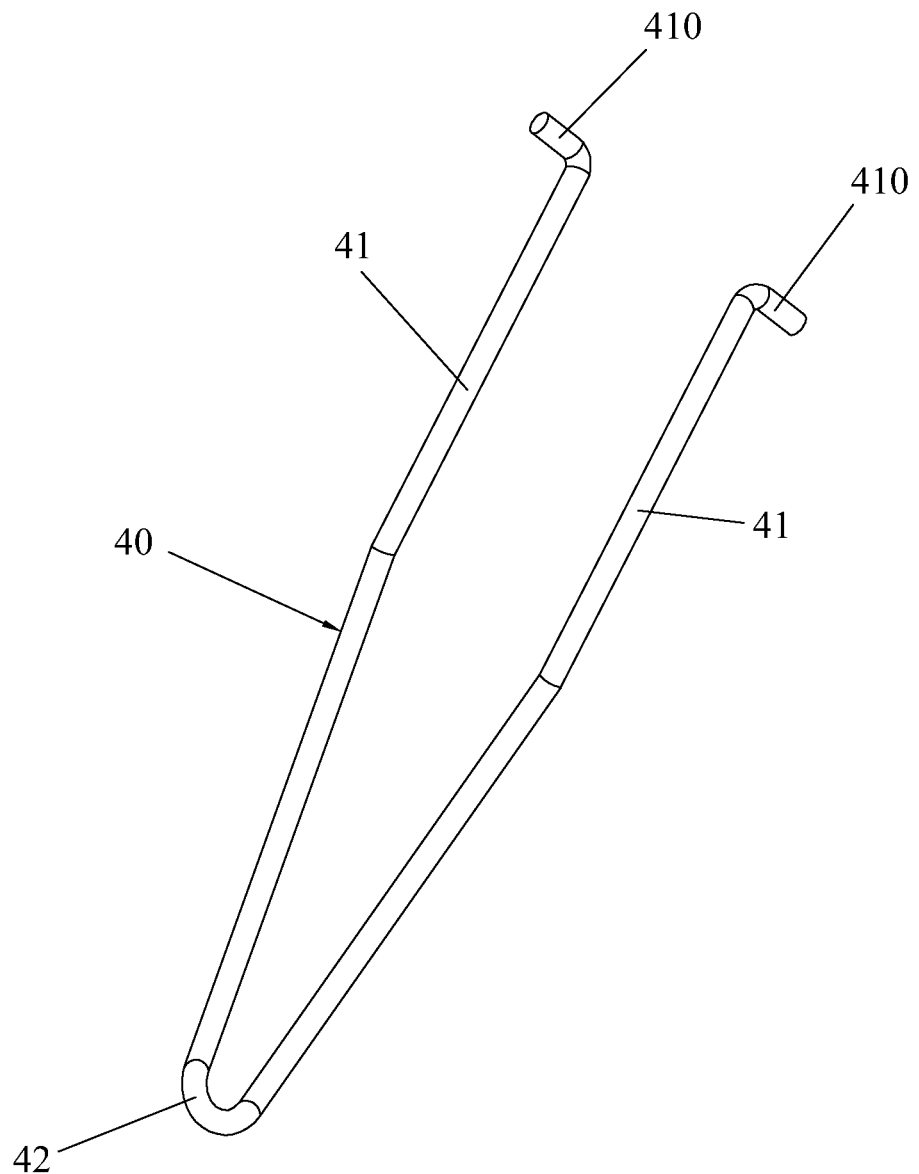
FIG. 11 is a schematic diagram of the connecting unit shown in FIG. 1.
Figure 12:
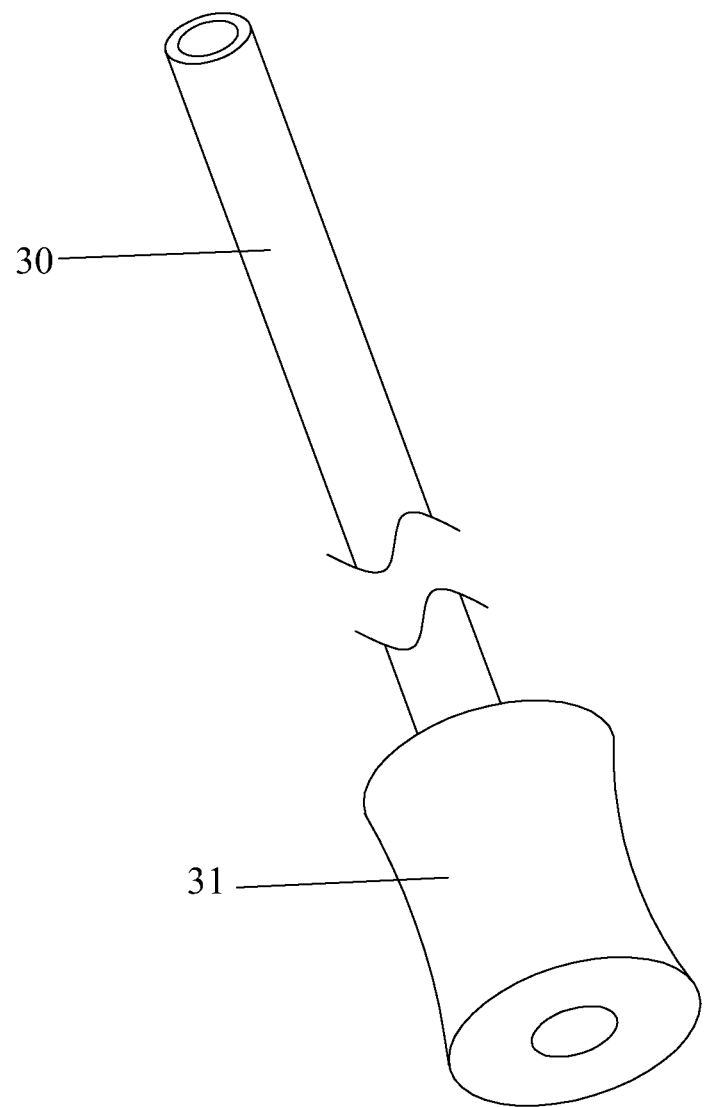
FIG. 12 is a schematic diagram of the protective sleeve shown in FIG. 1, with a handle arranged thereon for operation.

Referring to FIGS. 2, 3 and 10, a traction unit 60 runs through and move longitudinally in the conveying unit 20 and the accommodation tube 12. One end of the traction unit is connected to the joint part 112 of the ligation component, the other end is connected to the operation rod 51 of the operation unit 50, so that the traction unit could control the movement of the ligation component 111 via the operation block 52. Moreover, the end of the traction unit which is connected to the joint part of the ligation component could deform. An abutment part is arranged on the traction unit, when the traction unit is pulled back, the abutment part is abutted against the contact portion of the connecting unit, then the bent portions of the legs are disengaged from the connection hole correspondingly under this pull force.

As an prefer embodiment, referring to FIG. 1, the traction unit 60 includes a first traction rod 61 and a second traction rod 62, and the first traction rod 61 is connected to the joint part 112 of the ligation component, while the second traction rod is connected to the operation rod 51.

The front end of the first traction rod 61 (which is connected to the joint part 112 of the ligation component) is a hook 611, which has a bending front portion 6111 and a back portion 6112. When the ligation component is pushed to outspread, the back portion 6112 is abutted against the joint part 112 of the ligation component; while the ligation component is pulled back or folded, the front portion 6111 is abutted against the joint part 112 of the ligation component. When the traction unit is continued to be pulled back after the ligation component is folded, the hook 611 (the front portion 6111) is pulled to deform or to be straightened out, so that the joint part 112 of the ligation component detaches from the hook 611.

The first traction rod 61 is connected to the second traction rod 62 longitudinally to form an overlap part 600, which forms a step part 63, and the step part 63 is the abutment part. When the traction unit 60 is pulled back, the abutment part 63 is abutted against the contact portion 42 of the connecting unit 40, then traction unit 60 is continued to be pulled back, the bent portion 410 of the connecting unit 40 deforms and detaches from the connection hole.

According to the embodiment, the first traction rod 61 is pieces structure with certain thickness, and the second traction rod 62 is a traction rod with smaller diameter (such as steel rod), so that the step part 63 is formed obviously, and the contacting surface of the abutment part is increased.

Figure 19B:
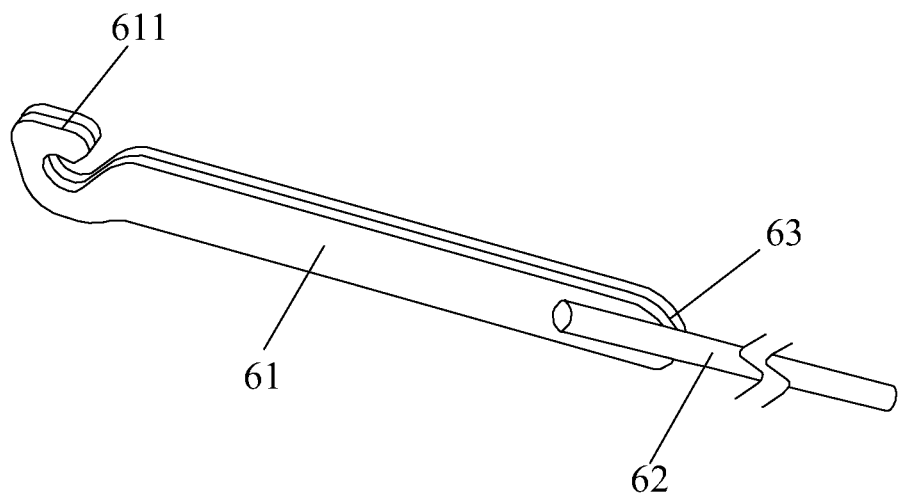
Figure 19C:
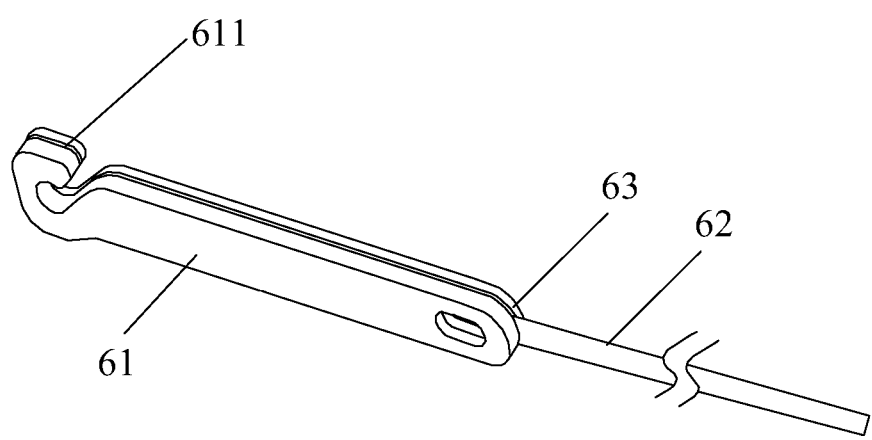
Figure 19D:
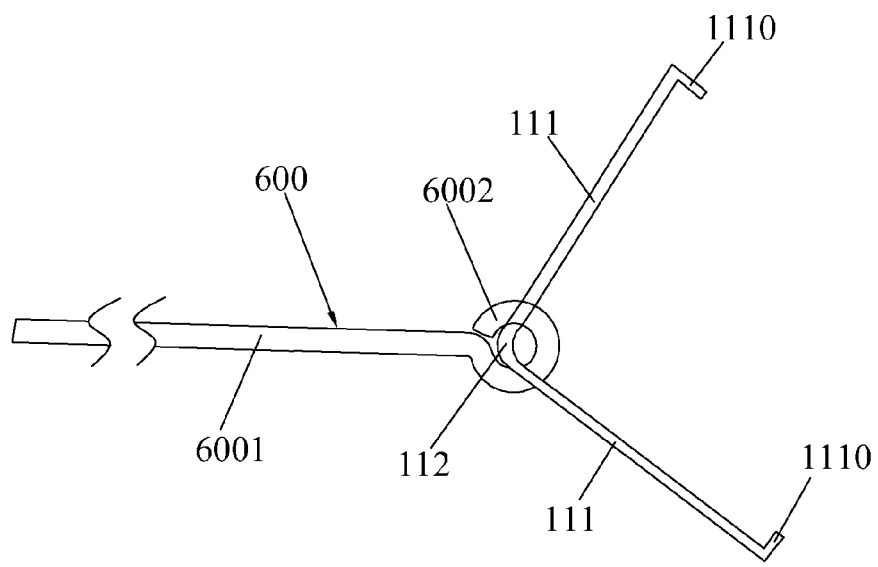

In other embodiments of the present invention, the traction unit could be other structure, such as the embodiments shown in FIGS. 19a-19d. Referring to FIG. 19a, the difference between the traction units shown in FIG. 19a and FIG. 10 is merely that: the first traction rod 61 of the traction unit shown in FIG. 19a is a structure with two side-by-side pieces, the front end of each piece has a hook, and two hooks are arranged in opposite directions. The difference between the traction units shown in FIG. 19a and FIG. 19b is merely that: FIG. 19b shows that two hooks are arranged in the same direction, and the second traction rod 62 is connected to one side of the first traction rod 61 which also has two side-by-side pieces. The structure of the traction unit shown in FIG. 19c is similar to that shown in FIG. 19b, and the difference is that the second traction rod 62 is connected between two pieces of the first traction rod 61. The traction unit shown in FIG. 19d is made by a single material, that is, the first traction rod and the second traction rod are molded in an integrated body; the traction unit 600 includes a traction rod 6001 and a hook 6002, and an abutment part is arranged on the traction rod 6001 (not shown in the figure), such as abutment block, abutment boss, etc.

In other embodiments of the present invention, any other structure which could make one end of the traction unit 60 disengage from the ligation unit when under certain force could be used in the present invention.

The ligation method applying the clamping and ligation device shown in FIG. 1 is given as follow by accompanying with drawings.

FIGS. 36-39 are schematic diagrams showing four steps of the ligation method applying the clamping and ligation device according to the present invention. Referring to FIGS. 36-39, the ligation method includes the following steps:

(1) The ligation component 11 of the clamping and ligation device 10 is folded in the accommodation tube 12, and the ligation unit 10 is contained in the protective sleeve completely. In the embodiment, as shown in FIG. 13, the stopper unit 70 is mounted on the flexible tube 21, so that the protective sleeve 30 moves forward to house the ligation unit 10 and the conveying unit 20 therein, and the position of the protective sleeve is limited, and could not move backward.

(2) The clamping and ligation device 10 is passed through a corresponding channel of an endoscope, and then to the operating position, and the operation unit 50, the handle and the back end of the protective sleeve 30, the back end of the flexible tube 21 are all exposed outside the living body.

(3) The stopper unit 70 is taken from the flexible tube 21; the whole operation unit 50 is pushed, so that the whole ligation unit is pushed out from the protective sleeve.

Figure 36:
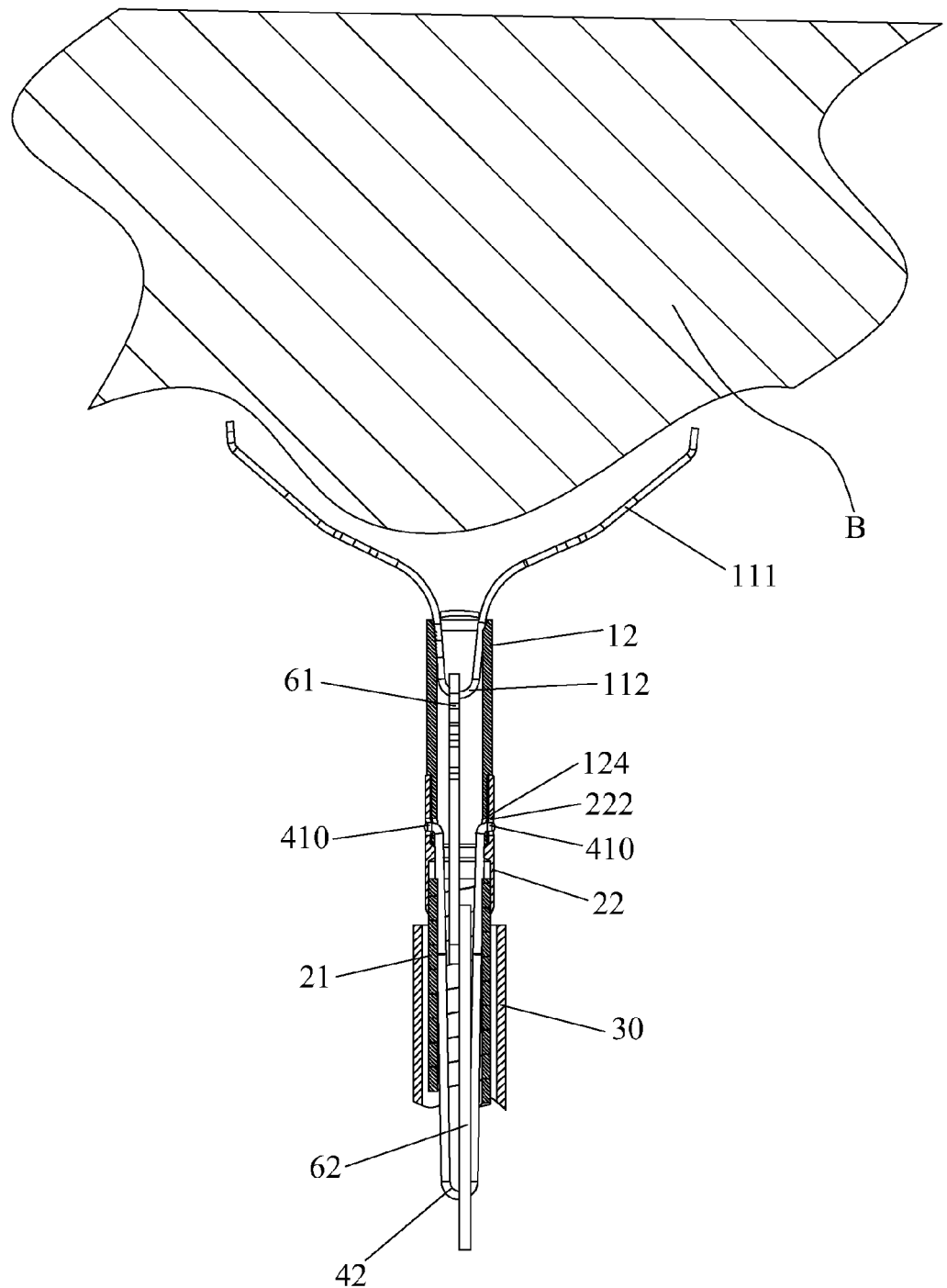
FIGS. 36-39 are schematic diagrams showing four steps of the ligation method applying the clamping and ligation device according to the present invention.

(4) the operation block 52 is pushed, and the operation block 52 then push the operation rod 51, so that the traction unit 60 moves forward to push the clamping arms 111 of the ligation component out of the accommodation tube 12 to spread out, and the living organism which is need to be ligated is arranged between the clamping arms 111, as shown in FIG. 36.

Figure 37:
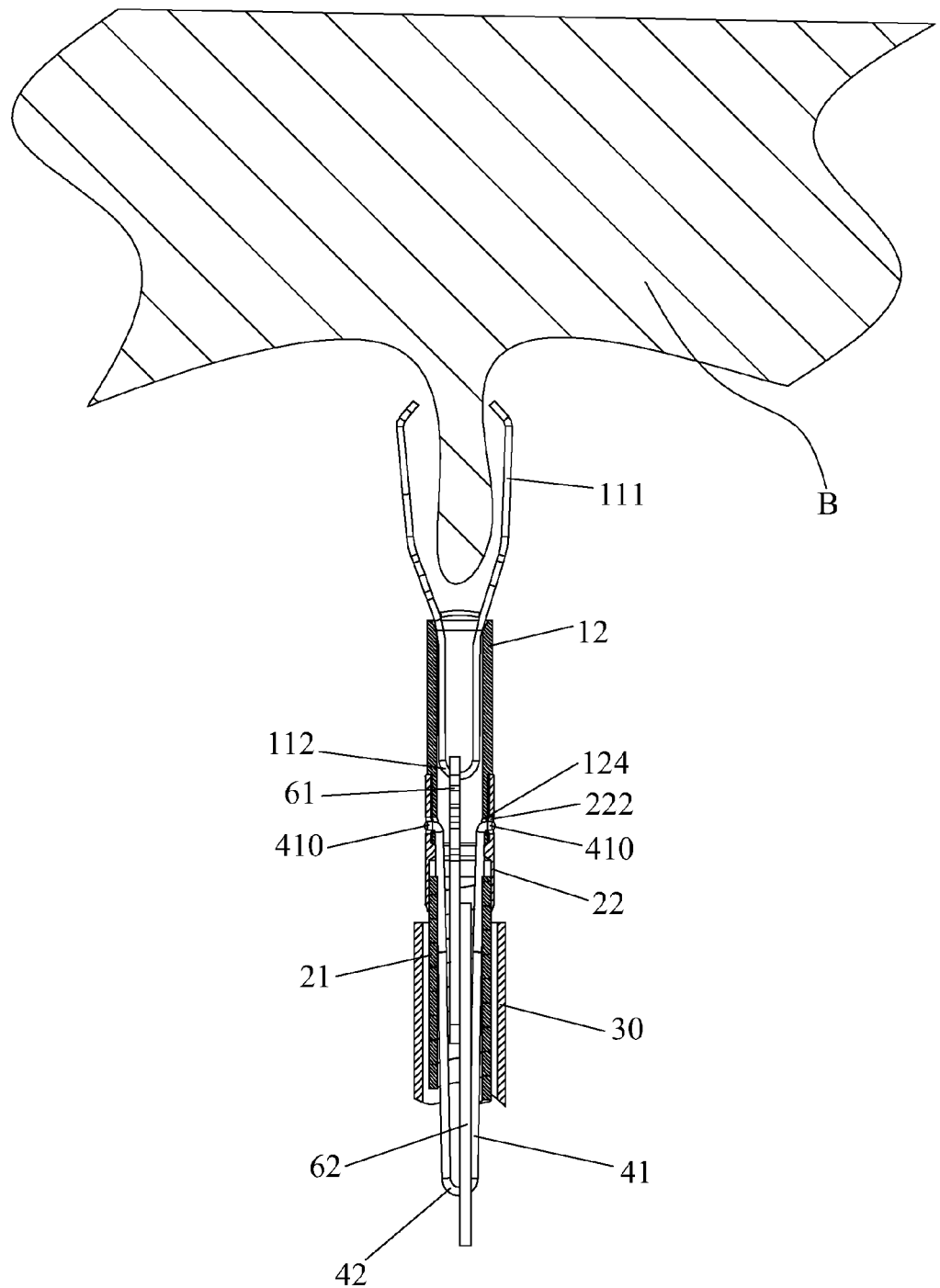

(5) The operation block 52 is pulled back, and then the ligation component 11 is pulled into and folded in the accommodation tube 12, at this time, the organism is clamped between the clamping arms 111, as shown in FIG. 37.

Figure 38:
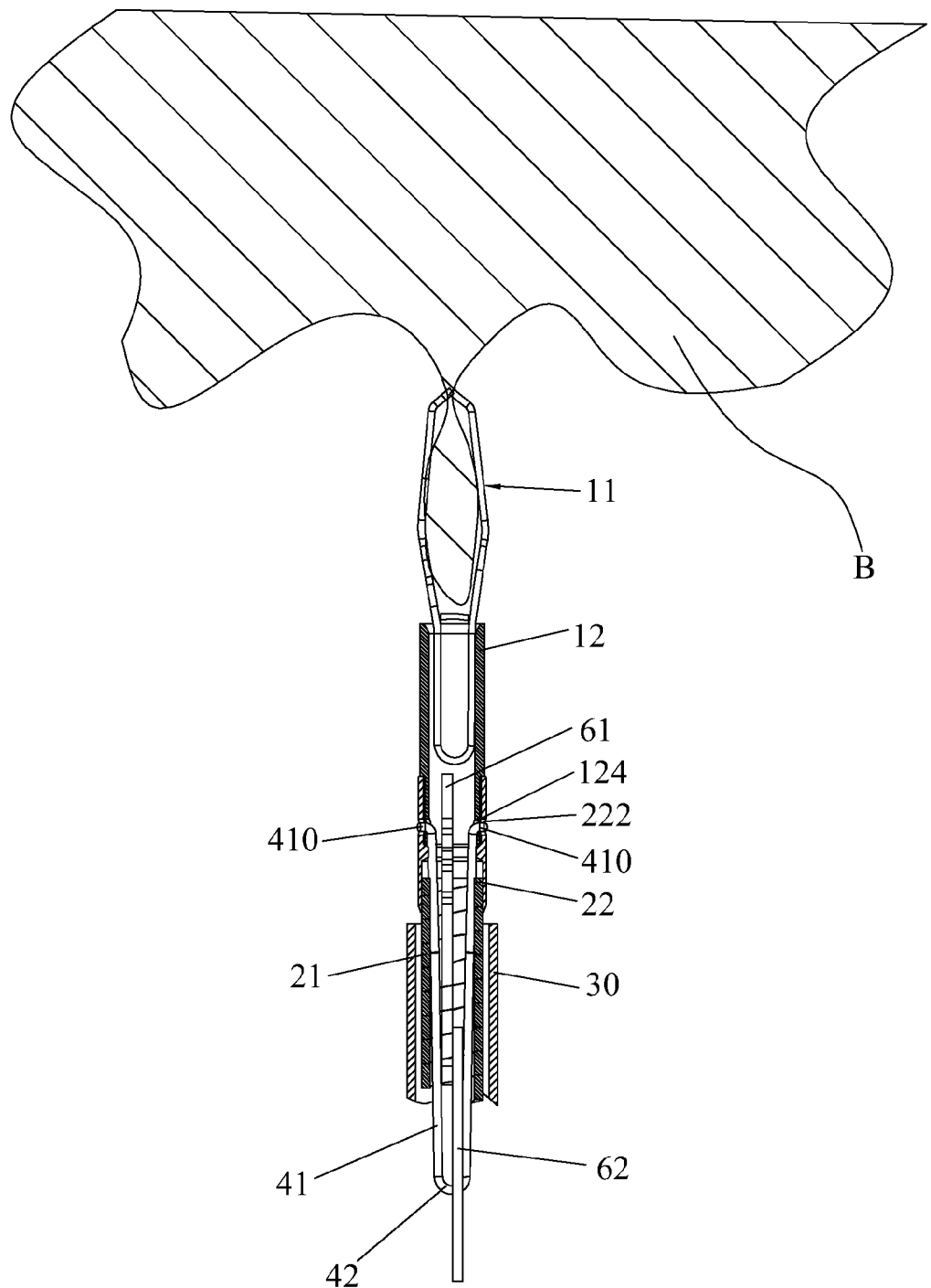

(6) The above steps (4)-(5) is repeated when the ligation is not ideal, until a desired effect is achieved;

(7) The operation block 52 is continued to be pulled back, the ligation unit 10 is pulled back, and the organism is clamped tightly between the clamping arms 111 of the ligation component. The pull is applied, and the end of the traction unit 60 which is connected to the ligation unit 10 deforms, that is, the hook 611 of the traction unit 60 deforms and is straightened out to detach from the joint part 112 of the ligation component, so that the traction unit 60 is detached from the ligation unit 10, as shown in FIG. 38.

Figure 39:
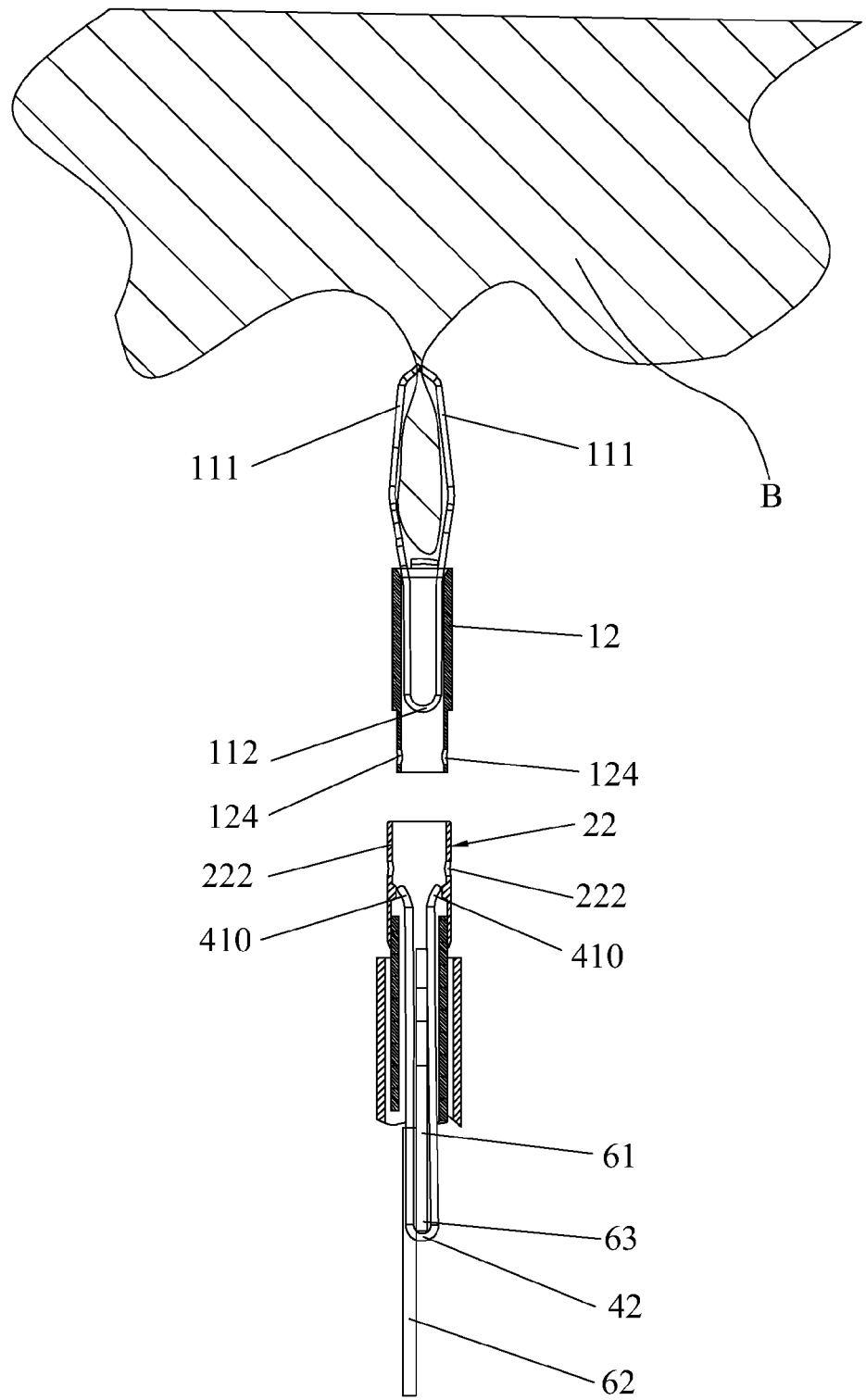

(8) The pull proceeds, the abutment part 63 of the traction unit 60 is abutted against the contact portion 42 of the connecting unit 40, and then the bent portion 410 of the leg 41 of the connecting unit is disengaged from the connection holes 222 and 124, and the accommodation tube is detached from the conveying unit, as shown in FIG. 39.

(9) The traction unit 60, the connecting unit 40, the conveying unit 20, the protective sleeve 30 and the operation unit 50 are pulled out from the living body, only the ligation unit 10 is remained in the living body. The ligation unit 10 could be remained in a digestive tract of a living body for some time and then falls off automatically to excrete from the living body.

In the above ligation method, when applied on a pull, the hook 611 of the traction unit is straightened out, and then the abutment part 63 of the traction unit is abutted against the contact portion 42 of the connecting unit 40, so that the bent portion 410 is disengaged from the connection holes 222 and 124.

In other embodiments, when the distance between the hook 611 of the traction unit and the abutment part 63 is longer and the hook 611 is straightened out slower, the pull is applied on the contact portion 42 via the abutment part 63, and then the bent portion 410 is disengaged from the connection holes 222 and 124, so that the ligation unit and the conveying unit are dropped off, the pull goes on, the hook 611 deforms and drops off. But the organism which is ligated would undergo larger pull, and this method is not as good as the above embodiment.

When the protective sleeve 30 is pulled out of the living body, the handle 301 is needed pulling; or the back end of the protective sleeve 30 is flattened, so the soft protective sleeve 30 is connected to the flexible tube 21, and then the handle 53 is pulled to pull the flexible tube 21, meanwhile, the protective sleeve 30 is pulled out from the living body.

All the above are the preferred embodiments of the present invention. It is to be understood that, for one skilled in the art, the invention is intended to cover various modifications and equivalent arrangements included within the principle of the invention.

What is claimed is:

1. A clamping and ligation device, characterized by comprising: a ligation unit, which comprises a ligation component and an accommodation tube in which the ligation component is housed, the ligation unit being capable of remaining in a digestive tract of a living body for some time and then falling off automatically to be excreted from the living body, the ligation component comprising at least two clamping arms arranged symmetrically, the clamping arms being connected to each other at the bottom thereof to form a joint part of the ligation component; a conveying unit, which is connected to an end of the accommodation tube, the conveying unit comprising a flexible tube and a sleeve which is mounted on an end of the flexible tube, the sleeve being engaged with the accommodation tube to form a junction, where a wall of the sleeve overlaps a wall of the accommodation tube, each of the sleeve and the accommodation tube has a connection hole and the connecting holes are aligned at the junction; a protective sleeve, which surrounds the conveying unit and the ligation unit, the conveying unit and the ligation unit being moved lengthwise in the protective sleeve, and the ligation unit being accommodated completely in the protective sleeve; a connecting unit, which comprises at least a leg, which has a contact portion formed at the bottom thereof and a bent portion at the top thereof, the bent portion being inserted into the connection hole formed on the conveying unit and the accommodation tube, so as to connect the conveying unit and the accommodation tube together, and the bent portion being disengaged from the connection hole when the leg is subjected to a longitudinal force; an operation unit, which comprises a main body, an operation rod and an operation block controlling the movement of the operation rod, and a back end of the flexible tube being mounted on the main body of the operation unit; and a traction unit, running through and moving longitudinally in the conveying unit and the accommodation tube, one end of the traction unit being connected to the joint part of the ligation component, the other end being connected to the operation rod of the operation unit, and the traction unit controlling the movement of the ligation component by the operation block; the end of the traction unit which is connected to the joint part of the ligation component being detachable from the joint part, the traction unit comprising an abutment part; when the traction unit is pulled back, the abutment part is abutted against the contact portion of the connecting unit, and then the bent portion of the leg is disengaged from the connection hole under the pull force.

2. The clamping and ligation device according to claim 1, characterized in that the sleeve of the conveying unit has a stepped hole, a step face is formed in a circumferential direction on an end of the accommodation tube to match with the stepped hole, and the stepped hole is engaged with the step face to make a wall of the sleeve overlap a wall of the accommodation tube.

3. The clamping and ligation device according to claim 1, characterized in that the flexible tube consists of flexible steel sheet or steel wire.

4. The clamping and ligation device according to claim 1, characterized in that the flexible tube consists of woven wire net or composites composed of woven wire net and plastic.

5. The clamping and ligation device according to claim 1, characterized in that the protective sleeve is flexible.

6. The clamping and ligation device according to claim 5, characterized in that the protective sleeve consists of PE, PP or PVC material.

7. The clamping and ligation device according to claim 1, characterized in that the ligation component is made by bending a single piece of material and forms two clamping arms, and two clamping arms are connected to each other to form the joint part of the ligation component.

8. The clamping and ligation device according to claim 1, characterized in that a clamping head is formed on the top of the clamping arm.

9. The clamping and ligation device according to claim 1, characterized in that the end of the traction unit which is connected to the ligation unit is a hook, which hooks the joint part of the ligation component; the hook deforms to detach from the joint part of the ligation component under a certain force.

10. The clamping and ligation device according to claim 1, characterized in that the traction unit comprises a first traction rod and a second traction rod which is connected to the first traction rod longitudinally to form an overlap part, and the overlap part forms a step part which forms an abutment part.

11. The clamping and ligation device according to claim 1, characterized in that the connecting unit is made by bending a single piece of material, and comprises two legs.

12. The clamping and ligation device according to claim 11, characterized in that two said legs are symmetrical and each has a bent portion at the top.

13. The clamping and ligation device according to claim 11, characterized in that two said legs are symmetrical and only one of them has a bent portion at the top.

14. The clamping and ligation device according to claim 1, characterized in that the connecting unit comprises at least three legs.

15. The clamping and ligation device according to claim 1, characterized in that the connecting unit comprises a leg.

16. The clamping and ligation device according to claim 1, characterized in that the connecting unit is a U-shaped structure made by bending a single piece of material, two arms of the U-shaped structure form two legs of the connecting unit, the bent portion is formed at the top of each leg; the bending portion in the middle of the U-shaped structure forms the contact portion.

17. The clamping and ligation device according to claim 1, characterized in that the protective sleeve comprises at least two channels, and the conveying unit and the ligation unit run through one of the channels.

18. The clamping and ligation device according to claim 1, characterized in that the clamping and ligation device further comprises a stopper unit, which is the removably mounted on one end of the flexible tube which is connected to the main body of the operation unit, the length of the stopper unit in a longitudinal direction of the flexible tube is greater than the length of the ligation unit in the longitudinal direction when the ligation component is folded, and the ligation unit is completely contained in the protective sleeve when the stopper unit is mounted on the flexible tube.

19. The clamping and ligation device according to claim 18, characterized in that the stopper unit comprises at least two flexible stopper arms which move in the same or in the opposite direction, each of the flexible stopper arms has a limit recess formed thereon to match with the flexible tube, and all the limit recesses form a limit hole for limiting the position of the flexible tube.

20. The clamping and ligation device according to claim 18, characterized in that the stopper unit comprises three flexible stopper arms which are arranged in row and coupled to each other at the bottom, the middle one of the flexible stopper arms moves in a certain direction, and the other two of the flexible stopper arms move in the opposite direction to the middle one, each of the flexible stopper arms has a limit recess formed thereon to match with the flexible tube, and three said limit recesses form a limit hole for limiting the position of the flexible tube.

21. The clamping and ligation device according to claim 1, characterized in that at least one separate plate is arranged on one end of the accommodation tube to separate the clamping arms, and the accommodation tube is provided with a chamfer to help the ligation component to spread and fold.

22. A ligation method applying the clamping and ligation device according to claim 1, characterized by comprising steps: (1) folding the ligation component of the clamping and ligation device in the accommodation tube, and containing the ligation unit in the protective sleeve completely;
(2) passing the clamping and ligation device through a channel which can hold an endoscope, and then to the operating position, wherein the operation unit, a back end of the flexible tube, and a back end of the protective sleeve are exposed outside the living body; (3) pushing the whole operation unit, and the ligation unit is pushed out from the protective sleeve;
(4) pushing the operation block, the operation block pushing the operation rod, and then the traction unit moving forward to push the ligation component spread out of the accommodation tube, and the position which needs to be ligated is arranged between the clamping arms;
(5) pulling back the operation block, and then the ligation component is pulled into the accommodation tube and is folded therein; (6) repeating steps (4)-(5) when the ligation is not ideal, until a desired effect is achieved; and (7) continue to pull back the operation block until the end of the traction unit which is connected to the ligation unit is detached from the ligation unit; the abutment part of the traction unit is abutted against the contact portion of the connecting unit, causing the bent portion of the leg of the connecting unit to disengage from the connection holes and causing the accommodation tube to detach from the conveying unit.

23. The ligation method according to claim 22, characterized in that the clamping and ligation device further comprises a stopper unit, which is removably mounted on one end of the flexible tube which is connected to the operation unit, the length of the stopper unit in a longitudinal direction of the flexible tube is greater than the length of the ligation unit in the longitudinal direction when the ligation component is folded, and the ligation unit is completely contained in the protective sleeve when the stopper unit is mounted on the flexible tube; during step (1), mounting the stopper unit on the flexible tube, and the ligation unit and the conveying unit is contained in the protective sleeve; during step (2), dismounting the stopper unit after the clamping and ligation device pass through the corresponding channel of the endoscope.

* * * * *